United States Patent
Simon et al.

(10) Patent No.: US 10,939,053 B2
(45) Date of Patent: Mar. 2, 2021

(54) SYSTEM AND METHOD FOR RADIO-FREQUENCY IMAGING, REGISTRATION, AND LOCALIZATION

(71) Applicant: Medtronic Navigation, Inc., Louisville, CO (US)

(72) Inventors: David A. Simon, Boulder, CO (US); Andrew Bzostek, Boulder, CO (US); Steven L. Hartmann, Superior, CO (US); Brandon Merkl, Lakewood, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 985 days.

(21) Appl. No.: 14/269,799

(22) Filed: May 5, 2014

(65) Prior Publication Data

US 2014/0240481 A1 Aug. 28, 2014

Related U.S. Application Data

(63) Continuation of application No. 12/767,449, filed on Apr. 26, 2010, now Pat. No. 8,717,430.

(51) Int. Cl.
*H04N 5/30* (2006.01)
*A61B 34/20* (2016.01)
(Continued)

(52) U.S. Cl.
CPC ............ *H04N 5/30* (2013.01); *A61B 34/20* (2016.02); *G01S 5/0252* (2013.01); *A61B 5/05* (2013.01);
(Continued)

(58) Field of Classification Search
CPC ............ H04N 5/30; H04N 2201/0079; G01S 5/0252; A61B 34/20; A61B 2090/364; A61B 5/05
(Continued)

(56) References Cited

U.S. PATENT DOCUMENTS 3,483,860 A 12/1969 Namerow
3,728,632 A 4/1973 Ross
(Continued)

FOREIGN PATENT DOCUMENTS

| EP | 0880763 A1 | 12/1998 |
|---|---|---|
| WO | WO-9729464 A1 | 8/1997 |
| WO | WO-2004107954 A2 | 12/2004 |

OTHER PUBLICATIONS

"StealthStation_S7_System® Information Center in the OR," (2009) Medtronic, Inc.
(Continued)

*Primary Examiner* — Joseph G Ustaris
*Assistant Examiner* — Jimmy S Lee

(57) ABSTRACT

A system for performing a medical procedure on a patient is provided. The system can include an imaging head defining a field of view relative to the patient. The imaging head can include at least one transmitter that emits at least one signal in the field of view, and at least one receiver that receives at least one reflected signal from the field of view. The at least one reflected signal received can be based on at least one electrical property of at least one material in the field of view. The system can further include a workstation, which can determine, based on the at least one reflected signal received by the at least one receiver, a location of at least one boundary of the material within the field of view. The system can include a display that displays an image of the location of the at least one boundary.

21 Claims, 11 Drawing Sheets

(51) Int. Cl.
*G01S 5/02* (2010.01)
*A61B 5/05* (2021.01)
*A61B 90/00* (2016.01)

(52) U.S. Cl.
CPC .............. *A61B 2090/364* (2016.02); *H04N 2201/0079* (2013.01)

(58) Field of Classification Search
USPC .......................................................... 348/77
See application file for complete search history.

(56) References Cited

U.S. PATENT DOCUMENTS

| | | | |
|---|---|---|---|
| 3,951,134 | A | 4/1976 | Malech |
| 4,085,740 | A | 4/1978 | Allen, Jr. |
| 4,123,759 | A | 10/1978 | Hines et al. |
| 4,135,131 | A | 1/1979 | Larsen et al. |
| 4,271,389 | A | 6/1981 | Jacobi et al. |
| 4,344,440 | A | 8/1982 | Aaby et al. |
| 4,427,982 | A | 1/1984 | Caprio |
| 4,513,748 | A | 4/1985 | Nowogrodzki et al. |
| 4,552,151 | A | 11/1985 | Bolomey et al. |
| 4,805,627 | A | 2/1989 | Klingenbeck et al. |
| 4,958,638 | A | 9/1990 | Sharpe et al. |
| 5,146,616 | A | 9/1992 | Tang et al. |
| 5,227,797 | A | 7/1993 | Murphy |
| 5,239,181 | A | 8/1993 | Sun et al. |
| 5,274,271 | A | 12/1993 | McEwan |
| 5,305,748 | A | 4/1994 | Wilk |
| 5,325,129 | A | 6/1994 | Henry et al. |
| 5,351,053 | A | 9/1994 | Wicks et al. |
| 5,361,070 | A | 11/1994 | McEwan |
| 5,363,050 | A | 11/1994 | Guo et al. |
| 5,551,158 | A | 9/1996 | Tyren et al. |
| 5,557,085 | A | 9/1996 | Tyren et al. |
| 5,576,693 | A | 11/1996 | Tyren et al. |
| 5,579,378 | A | 11/1996 | Arlinghaus, Jr. |
| 5,592,939 | A | 1/1997 | Martinelli |
| 5,668,555 | A | 9/1997 | Starr |
| 5,687,169 | A | 11/1997 | Fullerton |
| 5,704,355 | A | 1/1998 | Bridges |
| 5,715,819 | A | 2/1998 | Svenson et al. |
| 5,739,752 | A | 4/1998 | Tyren |
| 5,807,257 | A | 9/1998 | Bridges |
| 5,829,437 | A | 11/1998 | Bridges |
| 5,913,820 | A | 6/1999 | Bladen et al. |
| 5,989,751 | A | 11/1999 | Cotte et al. |
| 6,018,297 | A | 1/2000 | Tyren |
| 6,061,589 | A | 5/2000 | Bridges et al. |
| 6,232,879 | B1 | 5/2001 | Tyren |
| 6,270,591 | B2 | 8/2001 | Chiriac et al. |
| 6,381,485 | B1 | 4/2002 | Hunter et al. |
| 6,421,550 | B1 | 7/2002 | Bridges et al. |
| 6,466,125 | B1 | 10/2002 | Richards et al. |
| 6,474,341 | B1 | 11/2002 | Hunter et al. |
| 6,662,036 | B2 | 12/2003 | Cosman |
| 6,864,826 | B1 * | 3/2005 | Stove ............... G01N 22/00 342/22 |
| 6,885,191 | B1 | 4/2005 | Gleman |
| 6,952,201 | B2 | 10/2005 | Fukushima et al. |
| 6,989,751 | B2 | 1/2006 | Richards |
| 7,068,981 | B2 | 6/2006 | Sim |
| 7,227,359 | B2 | 6/2007 | Ma |
| 7,379,769 | B2 | 5/2008 | Piron et al. |
| 7,471,765 | B2 | 12/2008 | Jaffray et al. |
| 7,529,398 | B2 * | 5/2009 | Zwirn ............... A61B 5/0046 382/131 |
| 7,570,791 | B2 | 8/2009 | Frank et al. |
| 7,599,730 | B2 | 10/2009 | Hunter et al. |
| 7,664,303 | B2 | 2/2010 | Zwirn et al. |
| 7,826,592 | B2 | 11/2010 | Jaffray et al. |
| 7,907,989 | B2 * | 3/2011 | Borgert ............... A61B 5/06 382/128 |
| 8,421,859 | B2 * | 4/2013 | Zhang ............... B60W 30/09 340/988 |
| 8,663,120 | B2 * | 3/2014 | Markowitz ........... A61B 34/20 600/508 |
| 8,717,430 | B2 | 5/2014 | Simon et al. |
| 8,816,855 | B2 * | 8/2014 | Kreiner ............... G01S 13/82 340/572.1 |
| 2003/0181170 | A1 | 9/2003 | Sim |
| 2004/0006268 | A1 | 1/2004 | Gilboa et al. |
| 2004/0024257 | A1 | 2/2004 | Vastra et al. |
| 2004/0077943 | A1 | 4/2004 | Meaney et al. |
| 2004/0097811 | A1 | 5/2004 | Smith et al. |
| 2004/0215071 | A1 | 10/2004 | Frank et al. |
| 2004/0249257 | A1 | 12/2004 | Tupin et al. |
| 2004/0249258 | A1 | 12/2004 | Tupin et al. |
| 2005/0085714 | A1 | 4/2005 | Foley et al. |
| 2005/0228294 | A1 | 10/2005 | Yamaki |
| 2005/0245814 | A1 | 11/2005 | Anderson et al. |
| 2006/0184160 | A1 | 8/2006 | Ozaki et al. |
| 2007/0110289 | A1 * | 5/2007 | Fu ............... G06K 9/32 382/128 |
| 2007/0238987 | A1 * | 10/2007 | Minai ............... A61B 1/041 600/424 |
| 2007/0249901 | A1 | 10/2007 | Ohline et al. |
| 2008/0269588 | A1 * | 10/2008 | Csavoy ............... A61B 6/5247 600/407 |
| 2008/0269602 | A1 * | 10/2008 | Csavoy ............... A61B 90/18 600/426 |
| 2010/0016709 | A1 | 1/2010 | Gilboa et al. |
| 2010/0141744 | A1 | 6/2010 | Amling et al. |
| 2010/0195883 | A1 | 8/2010 | Patriarche et al. |
| 2010/0204563 | A1 | 8/2010 | Stodilka et al. |
| 2010/0268458 | A1 * | 10/2010 | Becker ............... G08G 5/0086 701/532 |
| 2011/0261180 | A1 | 10/2011 | Simon et al. |

OTHER PUBLICATIONS

"StealthStation® TRIA™ plus Treatment Guidance System," brochure, Medtronic Surgical Navigation Technologies (2004) 2 pages.
"Task 4 White Paper Automatic Identification of Medical Devices Final Version," Prepared for Food and Drug Administration Center for Devices and Radiological Health, (Aug. 17, 2005) Project Office: Brockton Hefflin, MD, MPH.
"TREON, StealthStation," brochure, Medtronic Surgical Navigation Technologies (2001) 8 pages.
Azevedo, Stephen, et al., "Micropower Impulse Radar: A New Pocket-size Radar That Operates up to Several years on AA Batteries and Costs only a Few Dollars is Stimulating Laboratory Research Efforts and a Variety of Industrial Products. Its Many Potential Uses Include Security, Rescue Operations, and Health Monitoring," Science and Technology Review, (Jan./Feb. 1996) pp. 17-29.
Baker-Jarvis, James, et al., "Measuring the Permittivity and Permeability of Lossy materials: Solids, Liquids, Metals, Building Materials, and Negative-Index Materials," National Institute of Standards and Technology, (2005) pp. 1-149.
Barrett, Terence, "History of UltraWideBand (UWB) Radar & Communications: Pioneers and Innovators," Progress in Electromagnetics Symposium 2000 (PIERS 2000), Cambridge, MA, (Jul. 2000) pp. 1-29.
Bioelectromagnetics Newsletter A Publication of the Bioelectromagnetics Society, Featuring James Lin, (May/Jun. 2003) No. 172, pp. 1-12.
Bonmassar, Giorgio, et al., "SAR Computations in a Realistic and High-Resolution Model of the Head with EEG Electrodes in Place," Martinos Center, Massachusetts General Hospital, Harvard medical School, (Feb. 1, 2002) pp. 1-3.
Bucholz, R.D., et al., Intraoperative Ultrasonic Brain Shift Monitor and Analysis, Stealth Station Marketing Brochure (1997) 2 pages.
Cleveland, Robert, et al., "Questions and Answers about Biological Effects and Potential Hazards of Radiofrequency Electromagnetic Fields," OET Bulletin 56, Fourth Edition, (Aug. 1999) pp. 1-36.
Cooper, Matthew, et al., "Accommodating Geometric and Thermodynamic Variability for Forward-Looking Infrared Sensors," SPIE

(56) References Cited

OTHER PUBLICATIONS

Aerosense '97 (SPIE's International Symposium on Aerospace/Defense Sensing, Simulation, & controls), Apr. 24, 1997.
Cuomo, Kevin, et al. "Ultra-Wideband Coherent Processing," The Lincoln Laboratory Journal vol. 10, No. 2, 1997, pp. 203-222.
Davis, Shakti, et al., "Ultrawideband Microwave Breast Cancer Detection: A Detection-Theoretic Approach Using the Generalized Likelihood Ratio Test," IEEE Transactions on Biomedical Engineering, vol. 52, No. 7, Jul. 2005, pp. 1237-1250.
El-Babli, Inas, "Reconstruction of Three Dimensional Inhomogeneous Bodies Using Unrelated Illumination," 1998 IEEE, IEEE 1998 Ph.D. Students Conference GRADCON'98 Proceedings; Winnipeg, MB, Canada; May 8, 1998, pp. 12-15.
Fear, Elise, "Microwave Detection of Breast Cancer: A Cylindrical Configuration for Confocal Microwave Imaging," Thesis Submitted in Partial Fulfillment of the Requirements for the Degree of Doctor of Philosophy at the University of Victoria, 2001, pp. 1-186.
Fear, Elise, et al., "Microwaves for Breast Cancer Detection," IEEE Potentials 2003, pp. 12-18.
Foley, "The StealthStation: Three-Dimensional Image-Interactive Guidance for the Spine Surgeon," Spinal Frontiers, Apr. 1996, pp. 7-9.
Formica, Domenic, et al. "Biological Effects of Exposure to Magnetic Resonance Imaging: An Overview," BioMedical engineering OnLine 3:11, Apr. 22, 2004, pp. 1-12.
Formica, Domenico, et al., "MRI & RF," Biomed Eng Online (2004).
Galkadowite, Senaratne, et al., "Microwave Signal Processing for Breast Cancer Detection," Massey University, 2004.
Golombeck, M., et al., "Calculation of the Dielectric Properties of biological Tissue Using Simple Models of Cell Patches," Institut fur Biomedizinische Technik, IBT, Universitat Karlsruhe (TH), Deutschland 2002.
Golombeck, Marc, "Physical Properties of Human Tissue" Oct. 11, 1999, pp. 1-3.
Hagness, S., et al., "Wideband Ultralow Reverberation Antenna for Biological Sensing," Electronics Letters Sep. 11, 1997, v. 33, No. 19, pp. 1594-1595.
Hamalainen, Matti, "Ultra Wideband Indoor Radio Channel Measurements," Centre for Wireless communications, FIN-90014 University of Oulu, Finland, 2002.
Hart, F., et al., "Penetration of Electric Fields into a Concentric-Sphere Model of Biological Tissue," Medical & Biological Engineering & Computing, Jan. 1986, v. 24 pp. 105-108.
He, Yun, "A Generalized Divergence Measure for Robust Image Registration," 2003 IEEE, pp. 1211-1220.
International Search Report and Written Opinion dated Aug. 16, 2011 for PCT/US/2011/033108 claiming benefit of U.S. Appl. No. 12/767,449, filed Apr. 26, 2010.
Kim, Jaehoon, et al, "Characterization of Implanted Antennas Inside a Human Head: SDGF and FDTD Techniques," URSI EMTS 2004, pp. 1209-1211.
Komarov, V., "Permittivity and Measurements," Encyclopedia of RF and Microwave Engineering, 2005 John Wiley & Sons, Inc. pp. 3693-3711.
Kotulska, Malgorzata, et al., "How Heterogenous Structure of tissue Effects Its Dielectric Characteristics," XII Marian Smoluchowski Symposium on Statistical Physics, Zakopane, Poland, Sep. 6-12, 1999, pp. 1085-1096.
Kshetrimayum, Rakhesh, "A Brief Intro to Metamaterials," 2004 IEEE, IEEE Potentials, pp. 44-46.
Lazebnik, Mariya, et al., "Tissue-Mimicking Phantom Materials for Narrowband and Ultrawideband Microwave Applications," IOP Publishing Ltd. 2005, pp. 4245-4258.

Li, Dun, et al., "Comparisons of Three Alternative Breast Modalities in a Common Phantom Imaging Experiment," Med. Phys. 30 (8), Aug. 2003, pp. 2194-2205.
Li, Xu, et al., "Numerical and Experimental Investigation of an Ultrawideband Ridged Pyramidal Horn Antenna with Curved Launching Plane for Pulse Radiation," 2003 IEEE, IEEE Antennas and Wireless Propagation Letters, vol. 2, pp. 259-262.
Lin, James C., "Microwave propagation in Biological Dielectrics with Application to Cardiopulmonary Interrogation" in Medical Applications of Mircrowave Imaging, Edited by Larsen, Lawrence E. and Jacobi, John H., pp. 47-58 (1986).
Lowery, Madeleine, et al., "A Multiple-Layer Finite-Element Mode of the Surface EMG Signal," IEEE Tranactions on Biomedical Engineering, V. 49, No. 5., May 2002, pp. 446-454.
Martinsen, Ørjan, "Interface Phenomena and Dielectric Properties of Biological Tissue," Encyclopedia of Surface and colloid Science, 2002 by Marcel Dekker, Inc., pp. 2643-2652.
MBBS "L10-USB-Pen Reader" MBBS S.A. (Version 1.02) 2005.
MBBS "L10-USB-TRAY Reader" MBBS S.A. (Version 1.02) 2005.
MBBS "MediTag™ metal 8.0" Data Sheet, MBBS S.A. (Version 1.02) 2005.
MBBS "MediTag™ plastic 5.6" MBBS S.A. (Version 1.03) 2005.
MBBS MediTag™ tray 70×40, MBBS S.A. (Version 1.03) 2005.
Meaney, Paul, "A Clinical Prototype for Active Microwave Imaging of the Breast," IEEE Transactions on Microwave Theory and Techniques, V. 48, No. 11, Nov. 2000, pp. 1841-1853.
Medtronic Navigation, "StealthStation® AXIEM™ Electromagnetic Navigation . . . ", 2005, www.stealthstation.com/physician/spine/library/axiem_ent.jsp, printed Aug. 19, 2006 (2 pages).
Miller, Leonard, "Why UWB? A Review of Ultrawideband Technology," National Institute of Standards and Technology, Apr. 2003, pp. 1-72.
Mohamadi, Fred, "Wafer-Scale Integration Brings Low Cost and a Small Footprint to Active Antenna Arrays," Feb. 2005, pp. 48-64.
Nilavalan, R., "Numerical Investigation of Breast Tumour Detection Using Multi-Static Radar," Electronics Letters, Dec. 11, 2003, v 39, No. 25.
Robertson, J., "High Dielectric Constant Oxides," Eur. Phys. J. Appl. Phys. 28, 2004, pp. 265-291.
Shi, Y., et al., "Microwave-Induced Thermal Imaging of Tissue Dielectric Properties," 2003, Dynamedia, Inc., pp. 109-121.
Shlager, Kurt, et al., "Optimization of Bow-Tie Antennas for Pulse Radiation," IEEE Transactions on Antennas and Propagation, v. 42, No. 7, Jul. 1994, pp. 975-982.
Steggles, Pete, et al., "The Ubisense Smart Space Platform, A Ubisense White Paper," Ubisense Limited, May 2005, pp. 1-5.
Time Domain PulsOn 200™ Ultra Wideband Evaluation Kit, Feb. 2003 Brochure.
Venkatesh, M., et al., "An Overview of Dielectric Properties Measuring Techniques," Canadian Biosystems Engineering, v. 47, 2005, pp. 7.15-7.30.
Wiesbeck, W., et al., "Wideband Antenna Characteristics for UWB Radio Systems," URSI EMTS 2004, pp. 852-854.
Xu, Minghua, et al., "Pulsed-Microwave-Induced Thermoacoustic Tomography: Filtered Backprojection in a Circular Measurement Configuration," Med. Phys. 29 (8), Aug. 2002, pp. 1661-1669.
Communication pursuant to Article 94(3) EPC dated Feb. 3, 2017 for European Application No. 117188169 corresponding to PCT/US2011/033108 claiming benefit of U.S. Appl. No. 12/767,449, filed Apr. 26, 2010.
Office Action regarding European Patent Application No. 11718816.9, dated Apr. 7, 2020.

* cited by examiner

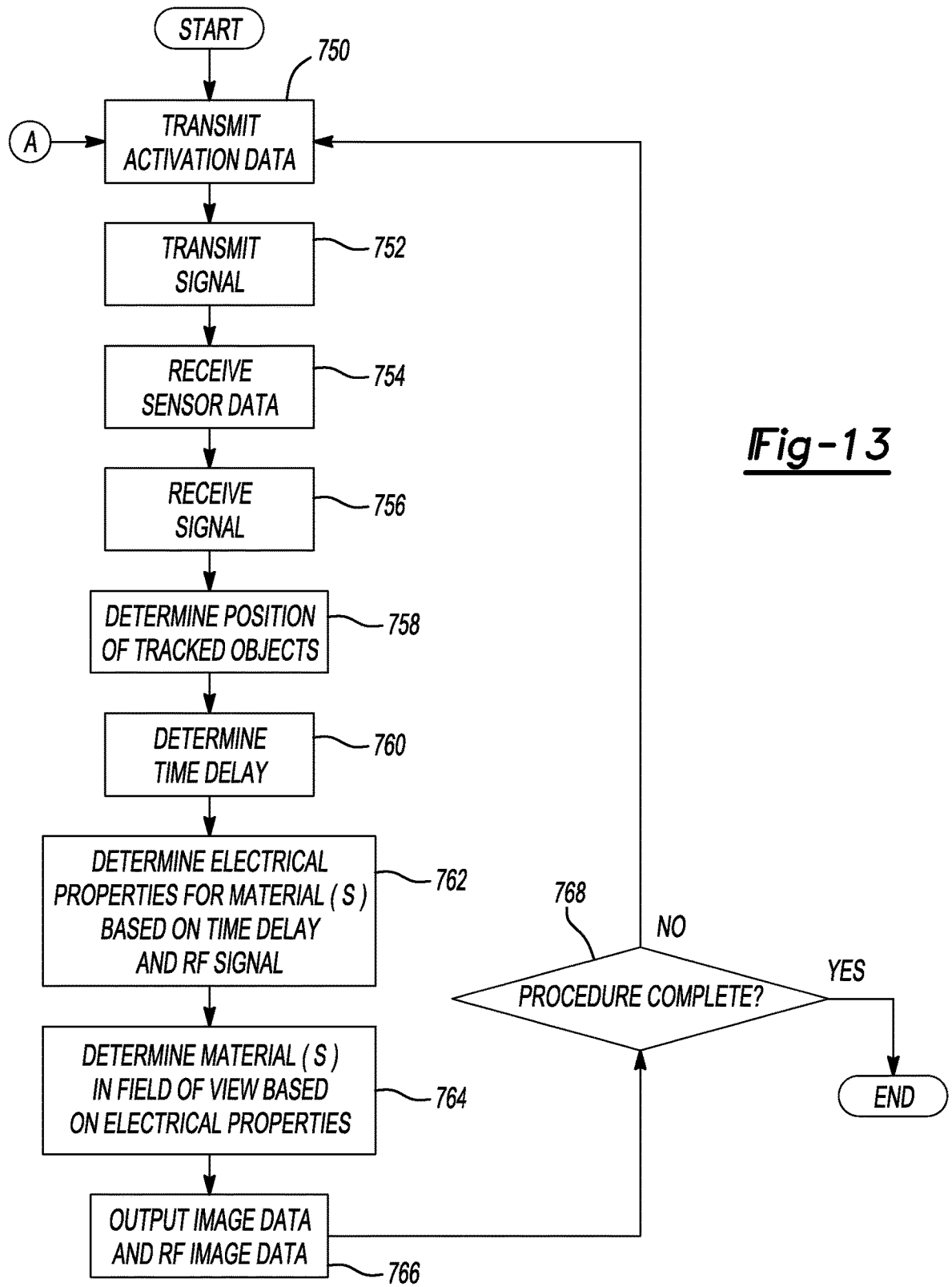

SYSTEM AND METHOD FOR RADIO-FREQUENCY IMAGING, REGISTRATION, AND LOCALIZATION

CROSS-REFERENCE TO RELATED APPLICATIONS

This application is a continuation of U.S. patent application Ser. No. 12/767,449 filed on Apr. 26, 2010. The disclosure of the above application is incorporated herein by reference.

FIELD

The present disclosure relates generally to navigated surgery, and more specifically, to systems and methods for the use of radio-frequency (RF) reflection, transmission, or scattering measurements (e.g. RF imaging) in a surgical procedure.

BACKGROUND

The statements in this section merely provide background information related to the present disclosure and may not constitute prior art.

Image guided medical and surgical procedures utilize patient images (image data) obtained prior to or during a medical procedure to guide a physician performing the procedure. Recent advances in imaging technology, especially in imaging technologies that produce highly-detailed, two, three, and four dimensional images, such as computed tomography (CT), magnetic resonance imaging (MRI), fluoroscopic imaging (such as with a C-arm device), positron emission tomography (PET), and ultrasound imaging (US) has increased the interest in navigated medical procedures.

At least some of the above mentioned imaging technologies can expose a patient and a surgeon to ionizing radiation. In addition, some of the above mentioned imaging technologies require contact between at least a portion of the imaging technology and the patient.

Thus, it may be desirable to provide an imaging system that is capable of imaging a patient without contacting the patient or exposing the patient or the surgeon to ionizing radiation.

SUMMARY

Provided is a system for performing a medical procedure on a patient. The system can include an imaging head defining a field of view relative to the patient. The imaging head can include at least one radio-frequency transmitter that emits at least one signal in the field of view, and at least one radio-frequency receiver that receives at least one reflected signal based on at least one electrical property of at least one material in the field of view. The system can also include a workstation having a control module, which can determine, based on the at least one reflected signal received by the at least one radio-frequency receiver, a location of at least one boundary of the at least one material within the field of view. The system can include a display that displays an image of the location of the at least one boundary.

Further provided is a system for performing a medical procedure on a patient. The system can include at least one tracking device, and a tracking system that tracks the at least one tracking device. The system can also include an imaging head that transmits at least one radio-frequency signal within a field of view and receives at least one reflected radio-frequency signal within the field of view. The system can include a navigation system, which can determine, based on the tracking of the tracking device and the at least one reflected radio-frequency signal, a location of the at least one tracking device within the field of view Also provided is a method for performing a medical procedure on a patient. The method can include positioning at least one imaging head relative to a patient to define a field of view, and emitting at least one radio-frequency signal from the imaging head into the field of view. The method can also include receiving at least one reflected radio-frequency signal from the field of view with the imaging head, and determining, based on the at least one reflected radio-frequency signal received from the field of view, at least one electrical property associated with at least one material within the field of view. The method can include determining, based on the at least one electrical property and the at least one reflected radio-frequency signal received from the field of view, a location of a boundary associated with the at least one material within the field of view.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 13 is an exemplary flowchart diagram that illustrates one of various control methods performed by the control module of FIG. 10.

DETAILED DESCRIPTION

Figure 1:
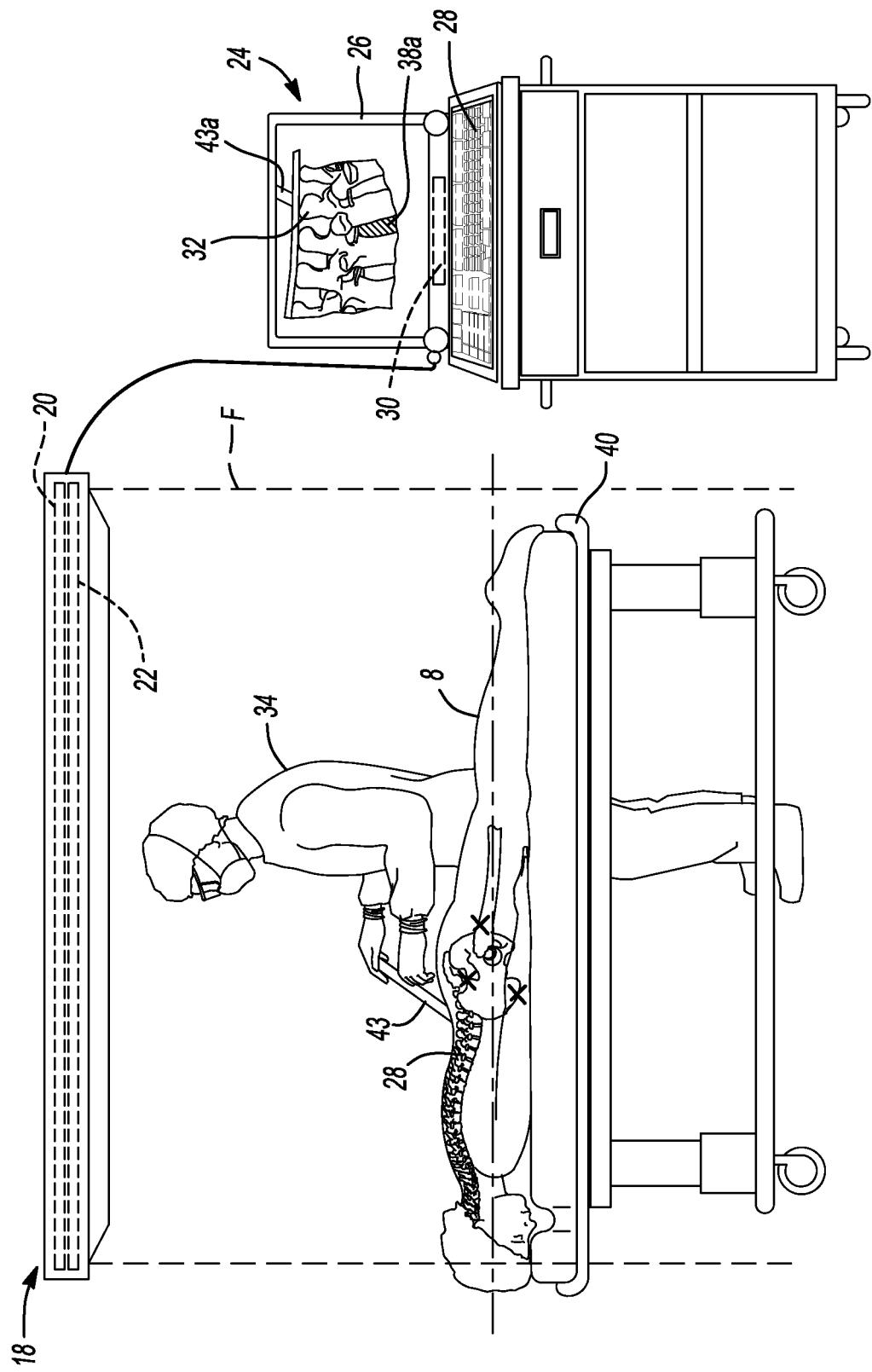
FIG. 1 is a schematic illustration of an exemplary RF imaging system for performing a surgical procedure on a patient according to various embodiments of the present disclosure.

The following description is merely exemplary in nature and is not intended to limit the present disclosure, application, or uses. It should be understood that throughout the drawings, corresponding reference numerals indicate like or corresponding parts and features. As indicated above, the present teachings are directed toward providing a system and method for a radio-frequency (RF) imaging assisted medical procedure. Exemplary medical procedures can include diagnostic procedures, surgical procedures, etc. It should be noted, however, that the present teachings could be applicable to any appropriate procedure in which it is desirable to determine a position of an object within an anatomy, for example. Further, as used herein, the term module can refer to an application specific integrated circuit (ASIC), an electronic circuit, a processor (shared, dedicated, or group) and memory that executes one or more software or firmware programs, a combinational logic circuit, and/or other suitable software, firmware programs or components that provide the described functionality. Therefore, it will be understood that the following discussions are not intended to limit the scope of the appended claims.

As will be discussed further herein, a navigation system can comprise a RF imaging system 12. The RF imaging system 12 can be used solely or in combination with a second imaging device, as will be discussed. In addition, as will be discussed, the RF imaging system 12 can also be used solely or in combination with a tracking system, such as an electromagnetic tracking system. The use of a RF imaging system 12 can provide for non-contact imaging of anatomy, and further, the use of the RF imaging system 12 does not expose the patient or users to ionizing radiation. As will be discussed, the RF imaging system 12 can also allow for the imaging of boundaries within an anatomy, such as a boundary between bone and soft tissue.

RF Imaging System

With reference to FIG. 1, the RF imaging system 12 can include an imaging head 18, which can be in communication with a workstation 24. In one example, the imaging head 18 can comprise a radio-frequency imaging head, which can include a reflective, transmissive, and/or scattering radio-frequency based measurement system. Generally, the imaging head 18 can transmit and receive signals within a field of view F. The imaging head 18 can be used in cooperation with the workstation 24 to determine the types of material(s) encountered for a particular depth within the field of view F, and to display a graphical representation of the material(s) as the material(s) are arranged within the field of view F. Generally, the imaging head 18 can be used to determine the presence of instruments, people (e.g. physician, patient), implants, fiducials, operating equipment, etc. that are within the field of view F of the imaging head 18, as will be discussed in greater detail herein.

A suitable imaging head 18 can comprise at least one transmitter, at least one receiver, etc., as will be discussed in greater detail herein. A suitable transmitter can comprise at least one antenna capable of transmitting radio-frequency (RF) energy. A suitable receiver can comprise at least one antenna capable of receiving radio-frequency energy. Antennas suitable for transmitting and receiving suitable energy are commercially available from Next RF, Inc. of Huntsville, Ala. A suitable imaging head 18 can also comprise a combination of multiple receiving and one or more transmitting antennas assembled into an array. Using algorithms in the known art, such as the algorithms discussed in U.S. Pat. No. 4,123,759 to Hines et. al., incorporated herein by reference, energy can be divided among the transmitting antennas to focus and/or steer energy transmitted by the antennas into particular spatial regions for the purposes of isolating any return signals. These algorithms may be implemented in a variety of ways, including but not limited to electrical hardware design, software control, or mechanical means. Further, using algorithms in the known art, such as those disclosed in U.S. Pat. No. 7,068,981 to Sim, incorporated herein by reference, energy received by the receiving antennas can be processed to focus and assign this energy to isolate signals from particular spatial regions.

As the imaging head 18 can be commercially available, the imaging head 18 will not be discussed in further detail herein. In one example, the imaging head 18 can include at least one radio-frequency (RF) transmitter 20 and at least one radio-frequency (RF) receiver 22, which can be integrated into a single radio-frequency (RF) sensor or antenna, for example.

Generally, the RF transmitter 20 can emit or transmit RF energy signals in a variety of forms, for example but not limited to: pulses, frequency chirps, single frequencies, continuous waves, and various signal compositions and modulations. These signals can occupy various frequency ranges, such as microwave wavelengths, which can range from about 1 centimeter to about 1 meter. In particular, pulses from the RF transmitter 20 can be transmitted at various bandwidths and pulse repetition frequencies (PRF), such as a bandwidth from 0.01 gigahertz to about 10 gigahertz, and PRF of 20-100 megahertz.

Typically, at least a portion of the energy transmitted by the RF transmitter 20 can be reflected from interfaces between materials with different electrical properties within the field of view F of the imaging head 18 and a portion of the reflected energy or the reflected signal can be received by the RF receiver 22. Generally, the round-trip time-of-flight of the RF signal from the transmitter to the receiver is determined by the distance traveled by the signal and the electrical properties of the material(s) passed through. In addition, the shape of returned signals can be affected by the electrical properties and geometric configuration of the material(s) passed through. In one example, with reference to Table 1, exemplary electrical properties of potential target materials are provided:

TABLE 1

Electrical Properties of Various Portions of the Anatomy

| Frequency MHz | Wavelength (cm) | Saline | | | Blood | | | Muscle/Skin | | |
| --- | --- | --- | --- | --- | --- | --- | --- | --- | --- | --- |
| | | Relative Dielectric constant | Conductivity | Wavelength in Tissue (cm) | Relative Dielectric Constant | Conductivity | Wavelength in Tissue (cm) | Relative Dielectric constant | Conductivity | Wavelength in Tissue (cm) |
| 433 | 69.3 | 70 | 1.72 | 7.5 | 62 | 1.2 | 8.2 | 53 | 1.43 | 8.5 |
| 915 | 32.8 | 70 | 1.8 | 3.8 | 60 | 1.4 | 4.1 | 51 | 1.6 | 4.4 |
| 2450 | 12.3 | 69 | 3.35 | 1.5 | 58 | 2.13 | 1.6 | 49 | 2.21 | 1.8 |

TABLE 1-continued

Electrical Properties of Various Portions of the Anatomy

| 5800 | 5.2 | 63 | 6.42 | 0.6 | 51 | 5.33 | 0.7 | 43 | 4.73 | 0.8 |
| 10000 | 3 | 53 | 17.2 | 0.4 | 45 | 11.7 | 0.4 | 40 | 10.3 | 0.5 |

| | Lung | | | Fat/Bone | | |
|---|---|---|---|---|---|---|
| Frequency MHz | Relative Dielectric Constant | Conductivity | Wavelength in Tissue (cm) | Relative Dielectric Constant | Conductivity | Wavelength in Tissue (cm) |
| 433 | 36 | 0.72 | 10.8 | 5.6 | 0.08 | 28.2 |
| 915 | 35 | 0.73 | 5.4 | 5.6 | 1 | 13.7 |
| 2450 | 32* | 1.32* | 2.2 | 5.5 | 16 | 5.2 |
| 5800 | 28* | 4.07* | 1 | 5.1 | 0.26 | 2.3 |
| 10000 | 25* | 9.08* | 0.6 | 4.5 | 0.44 | 1.4 |

*= extrapolated value

For further detail regarding the data illustrated in Table 1, see Lin, J. C., 1986: Microwave propagation in biological dielectrics with application to cardiopulmonary interrogation. In Medical Applications of Microwave Imaging Ed by L. E. Larsen and J. H. Jacobi, IEEE Press, NY, pp. 47-58, each incorporated by reference herein.

With continued reference to FIG. 1, the workstation 24 can be in communication with the RF transmitter 20 and the RF receiver 22 to determine the location of interfaces or boundaries between and electrical properties of material(s) encountered by the RF signal(s). The workstation 24 can include a display 26, a user input device 28 and a control module 30. The workstation 24 can also include or be connected to an image processor, navigation processor, and memory to hold instruction and data. The workstation 24 can provide facilities for displaying RF image data 32 on the display 26, saving, digitally manipulating, or printing a hard copy image of the received RF image data 32.

The user input device 28 can comprise any device that can enable a user to interface with the workstation 24, such as a touchpad, touch pen, touch screen, keyboard, mouse, voice-activated wireless mouse, or a combination thereof. The user input device 28 allows a physician or user 34 can also provide inputs to control the imaging head 18 or adjust the display settings of the display 26.

Figure 1A:
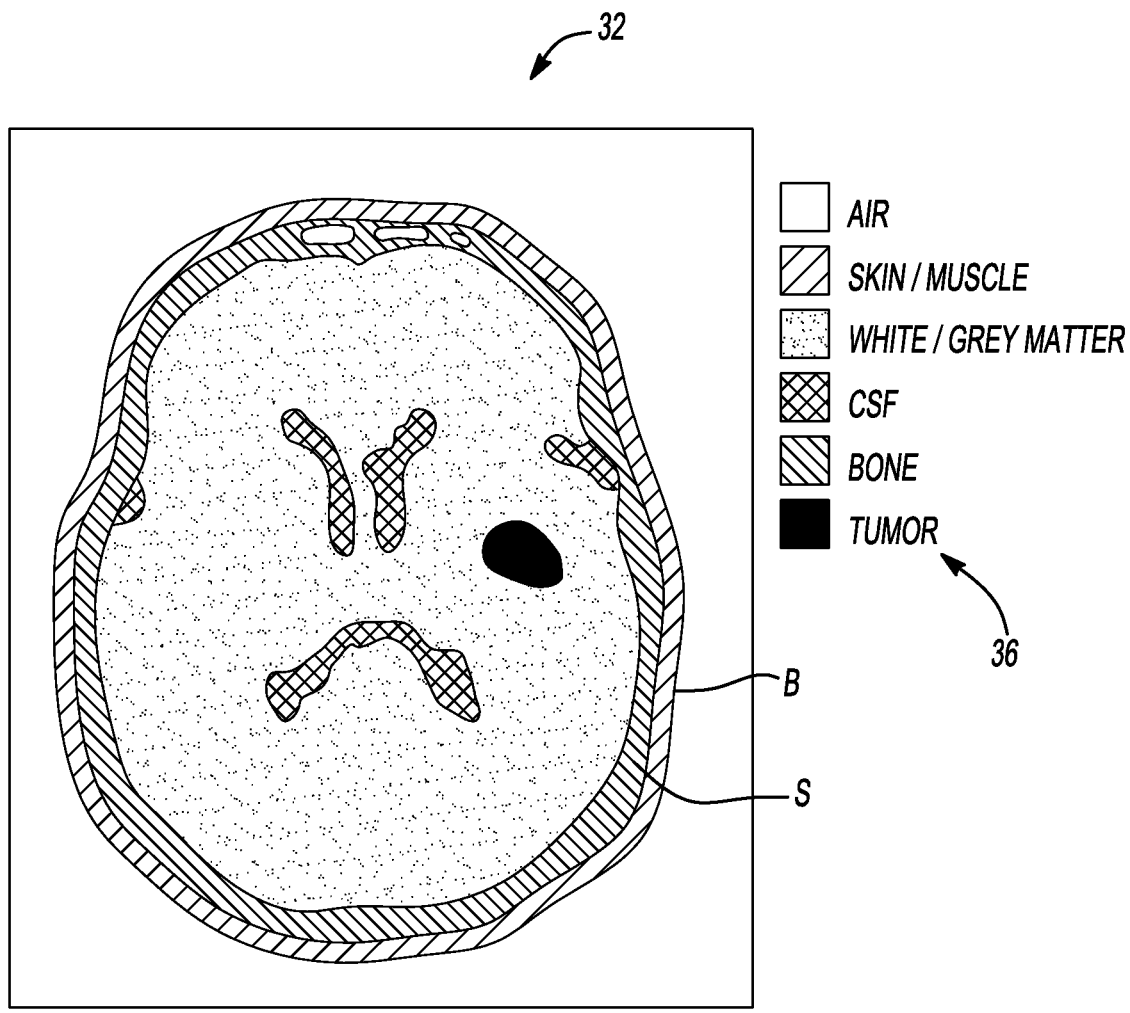
FIG. 1A is a schematic illustration of an exemplary RF image.

The control module 30 can output RF image data 32 to the display 26. The RF image data 32 can include a graphical representation of the boundaries and types of material(s) encountered by the RF signal, which can be displayed as the RF image data 32 on the display 26. In one example, the RF image data 32 can comprise at least one boundary, shaded area, icon, etc., which can denote the material(s) traversed by the signal, as illustrated in FIG. 1A.

Aggregating data from one or more signals, based on the return time for the signal(s), the shape or other characteristics of the return signal(s), the known shape of the transmitted signal(s), the known locations of the transmitter(s) and receiver(s), the known electrical properties of each material and optionally a model for expected spatial relationships among the material(s), the workstation 24 can determine the type and location of material(s) encountered by the signal.

The locations of the transmitter(s) and receiver(s) can be determined using a variety of means, including but not limited to: manufacturing specification, static measurement such as using direct physical measurement, manipulation with a physical mechanism such as a rotation stage, and dynamic measurement for example using a tracking system such as an electro-magnetic tracking system, further discussed herein.

Exemplary material(s) encountered by the signal can comprise saline, blood, skin, muscle, cancerous tissue, lung tissue, fat tissue, bone, polymer, metal, metal alloy, etc. Once the workstation 24 has determined the type and location of material(s) encountered by the signal(s), the workstation 24 can generate the RF image data 32 for display on the display 26.

Models for expected spatial relationships among materials can include, but are not limited to, information such as: the expected layers to be encountered by the signal, expected orientations of interfaces, and information determined by alternative imaging means such as 3D computed tomography (CT) or magnetic resonance (MR) imaging.

After a first determination of type and location of the material(s) encountered by the RF signal(s), measurements from additional signals can be used to refine this information. These additional signals can have RF parameters which are different than the first signal(s).

In addition, since the electrical properties of materials can vary based on secondary attributes of the material, including for example, water content, disease state, or density, the workstation 24 can also determine the secondary attributes for the material(s) encountered by the RF signal. The workstation 24 can output this data as additional image data 36 for display on the display 26. The additional image data 36 can comprise a secondary attribute metric for the material(s) encountered by the signal, and can be superimposed on the RF image data 32, if desired.

Further, localized variation of the electrical properties of materials can lead to an observed texture within a region of the material(s) encountered by the RF signal. This texture can be analyzed to measure, identify and locate sub-structure(s), and additional secondary attributes of the material(s).

In addition, by comparing textures and boundaries from multiple collections of RF signals sharing a common sub-region, dynamic information, such as motion or change in location of material(s), structure(s) and sub-structure(s) can be measured. Based on this information, additional images can be generated which reflect this dynamic information or data. Further, this dynamic information can also be used to measure cyclic and acyclic temporal attributes. These attributes can include, but are not limited to: cardiac and pulmonary cycles, injection bolus tracking, tracking of fiducials, biomechanical kinematics, disease progression, and implant dynamics and wear. This information can be displayed to the user on the display, or used to generate additional images.

With reference to FIG. 1, in one example, the imaging head 18 can be suspended above an operating table 40. In this example, the imaging head 18 can detect the presence of at least the user 34, the patient 8, and the operating table 40. In addition, due to the known electrical properties of the anatomy, the imaging head 18 can detect the boundary between the skin S of the patient 8, and the bone B of the patient 8, which can be displayed on the display as the RF image data 32 (FIG. 1A). This can enable the user 34 to visualize the boundary between the skin S and the bone B in a non-invasive manner.

Further, the known electrical properties of the anatomy can allow the workstation 24 to determine if a tissue imaged by the imaging head 18 is healthy or unhealthy. In this regard, cancerous tissue or tumors can have dielectric properties that can be substantially distinct from the dielectric properties associated with healthy or non-cancerous tissues. Thus, the workstation 24 can be used to determine if unhealthy or cancerous tissue has been encountered by the signal of the imaging head 18, as shown in FIG. 1A.

In addition, with reference to FIG. 1, the imaging head 18 could also be used to determine the location of metal, metal alloys, polymeric or other various man-made materials in the path of the signal due to the known electrical properties of such materials. In one example, the imaging head 18 can be used to determine the position of an implant 38 and an instrument 43 within the field of view F of the imaging head 18. The implant 38 can comprise any suitable implant, such as a spinal implant, orthopedic implant, implantable cardiac device, drug delivery device, etc., which can generally be composed of a metal, metal alloy or material having a known electrical properties. Given the known electrical properties of the implant 38, and known RF parameters of the signal, the control module 30 can determine a position of the implant 38 within the field of view of the imaging head 18, which can be output to the display 26 as implant data 38a. The implant data 38a can be superimposed on the RF image data 32 on the display 26, if desired.

Similar to the implant 38, the position of the instrument 43 within the field of view F of the imaging head 18 can be determined by the workstation 24. In this regard, the instrument 43 can comprise any suitable instrument, such as a guide wire, arthroscopic system, cardiac lead, deep-brain stimulator (DBS) probe, impacter, stylet, reamer, driver, tap, drill, etc. Given the known electrical properties of the instrument 43 and the known RF parameters of the signal, the control module 30 can determine a position of the instrument 43 within the field of view F of the imaging system 18, which can be output as instrument data 43a to the display 26. The instrument data 43a can be superimposed on the RF image data 32 on the display 26, if desired.

Figure 2:
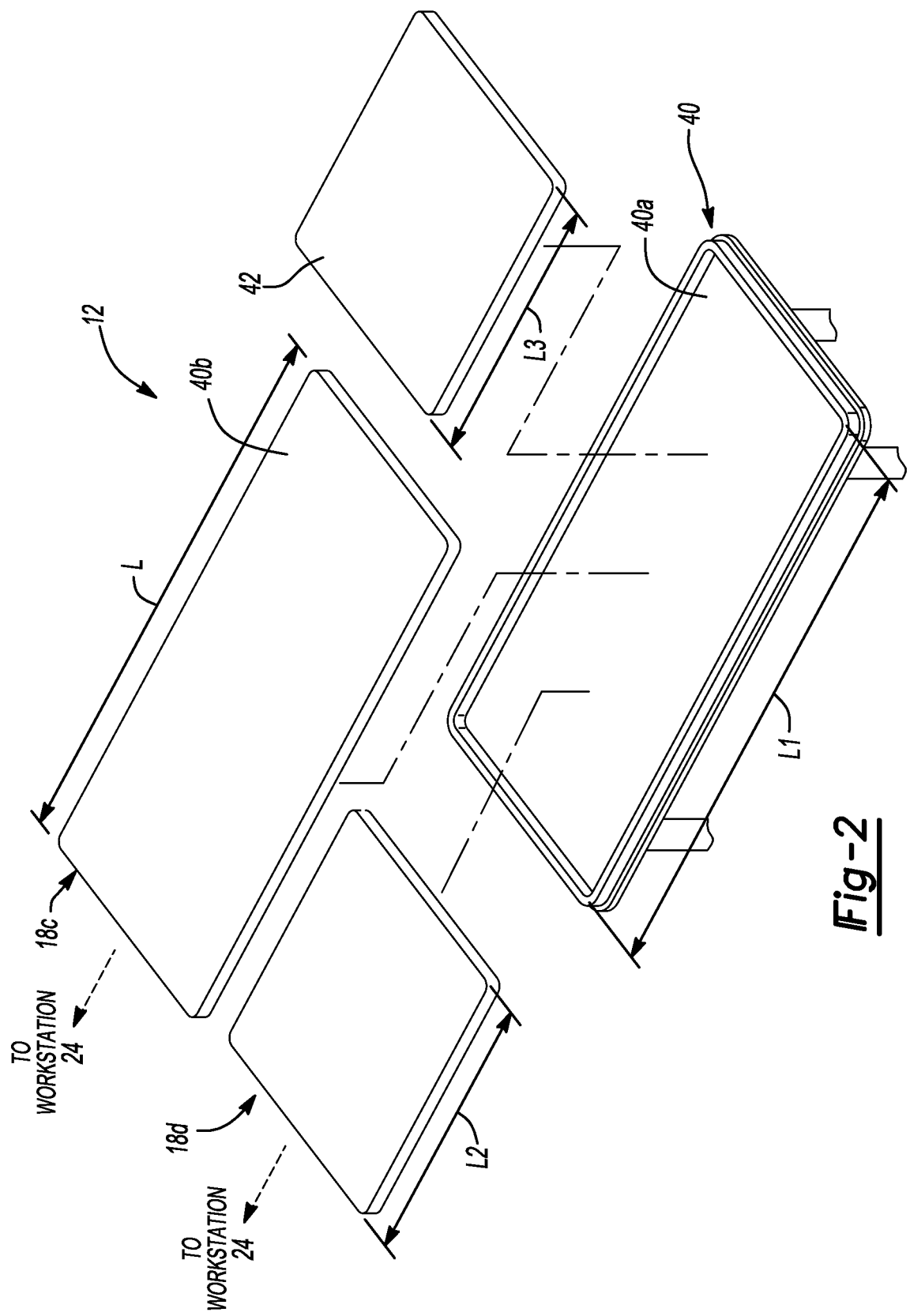
FIG. 2 is a schematic illustration of one of various embodiments for the RF imaging system of FIG. 1.

In one of various examples, with reference to FIG. 2, the imaging head 18 could be configured to be received within at least a portion of the operating table 40. In this regard, the operating table 40 can include at least one recess 40a, which can be configured to receive an imaging head 18c. The recess 40a can generally be defined about a perimeter of the operating table 40, so that the imaging head 18c can be positioned directly underneath at least a portion of the patient 8.

In one example, the imaging head 18c can be sized to fit within the recess 40a so that the imaging head 18c is positioned under a substantial portion of the patient 8. Thus, in this example, the imaging head 18c can substantially encompass an entire surface 40b of the operating table 40. In other words, the imaging head 18c can have a length L, which can be about equal to a length L1 of the operating table 40. This can enable the user 34 to visualize the anatomy of the patient 8 disposed over the length L of the imaging head 18c, without requiring the use of ionizing radiation.

In another of various examples, as also illustrated in FIG. 2, an imaging head 18d can cooperate with a non-imaging insert 42 to form the surface 40 of the operating table 40. In this example, the imaging head 18d can have a length L2, which can be about half the length L1 of the operating table 40. The non-imaging insert 42 can have a length L3, which can be about half the length L1 of the operating table 40, so that the imaging head 18d and the non-imaging insert 42 can be received with in the recess 40a to form a surface of the operating table 40. In this example, the imaging head 18d can be positioned under a selected portion of the anatomy, which can generally be the portion of the anatomy subjected to the surgical procedure. In one example, the imaging head 18d can be positioned beneath a skull of a patient for imaging during a neurosurgical procedure. In another example, the imaging head 18d can be positioned beneath the legs of a patient for imaging during a knee replacement procedure. In both of the above examples, the non-imaging insert 42 can be positioned within the recess 40a opposite the imaging head 18d to form a uniform surface for the operating table 40.

Figure 3:
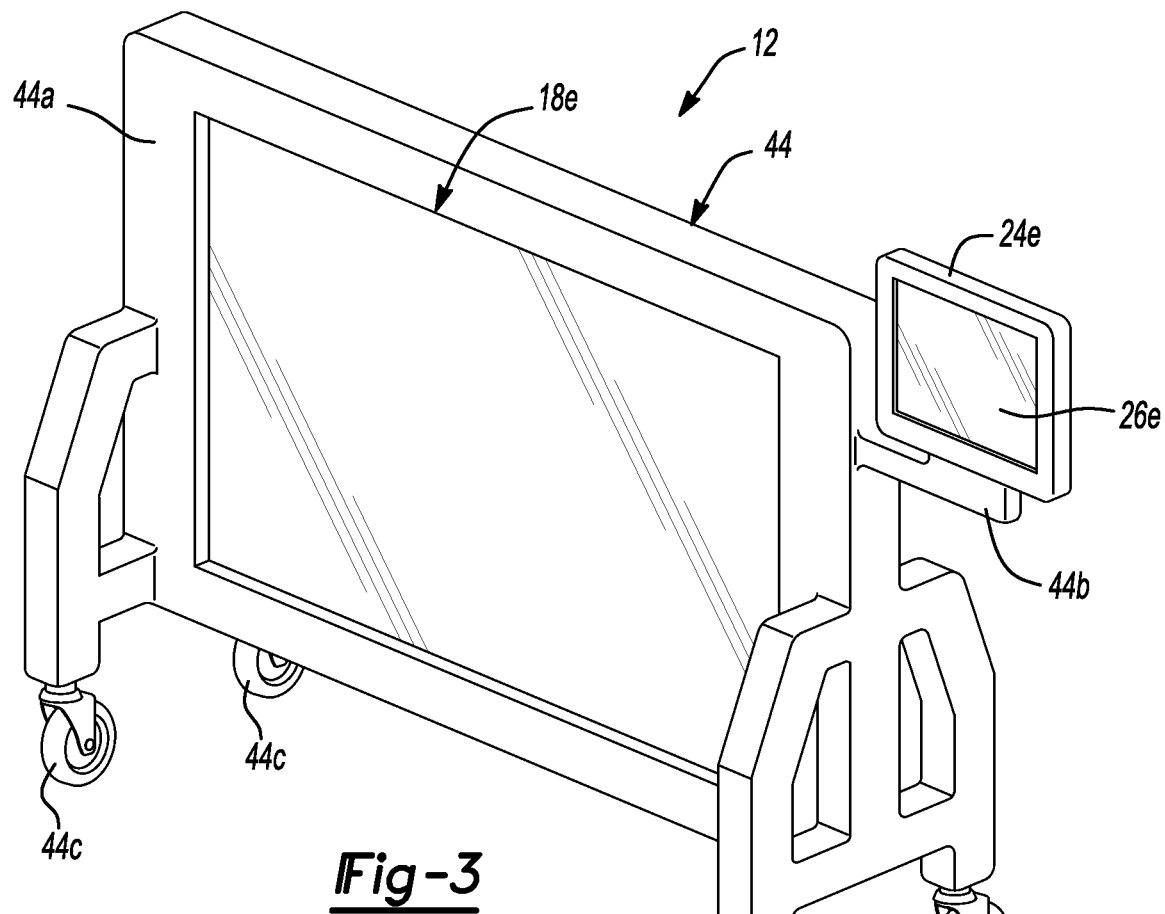
FIG. 3 is a schematic illustration of one of various embodiments for the RF imaging system of FIG. 1.

With reference to FIG. 3, in another of various examples, an imaging head 18e can be coupled to a movable frame 44. The movable frame 44 can also support a workstation 24e and a display 26e. The movable frame 44 can include a body 44a, an arm 44b and one or more movable members 44c. The body 44a can support and couple the imaging head 18e to the movable frame 44. The imaging head 18e can be coupled to the body 44a via any suitable technique, such as mechanical fasteners, press-fitting, etc. In addition, the imaging head 18e could be integrally formed with the body 44a, if desired.

The arm 44b can support the workstation 24e and display 26e. In this example, the workstation 24e could be located within a portion of the display 26e, however, the workstation 24e could be a separate unit, which could also be supported on the movable frame 44, via any suitable mechanism. The display 26e can be movable or rotatable about the arm 44b, so that the display 26e can be moved into a desired viewing position.

The movable members 44c can be coupled to the body 44a. The movable members 44c can comprise casters, rollers, wheels, etc. The movable members 44c can allow the movable frame 44 to be portable so that the movable frame 44 can be moved for use in various areas of a hospital, for example. Thus, the movable frame 44 can allow the imaging head 18e to comprise a portable imaging unit, which can be transported to various areas within a hospital, doctor's office, etc. to maximize the use of the imaging head 18e.

Figure 4:
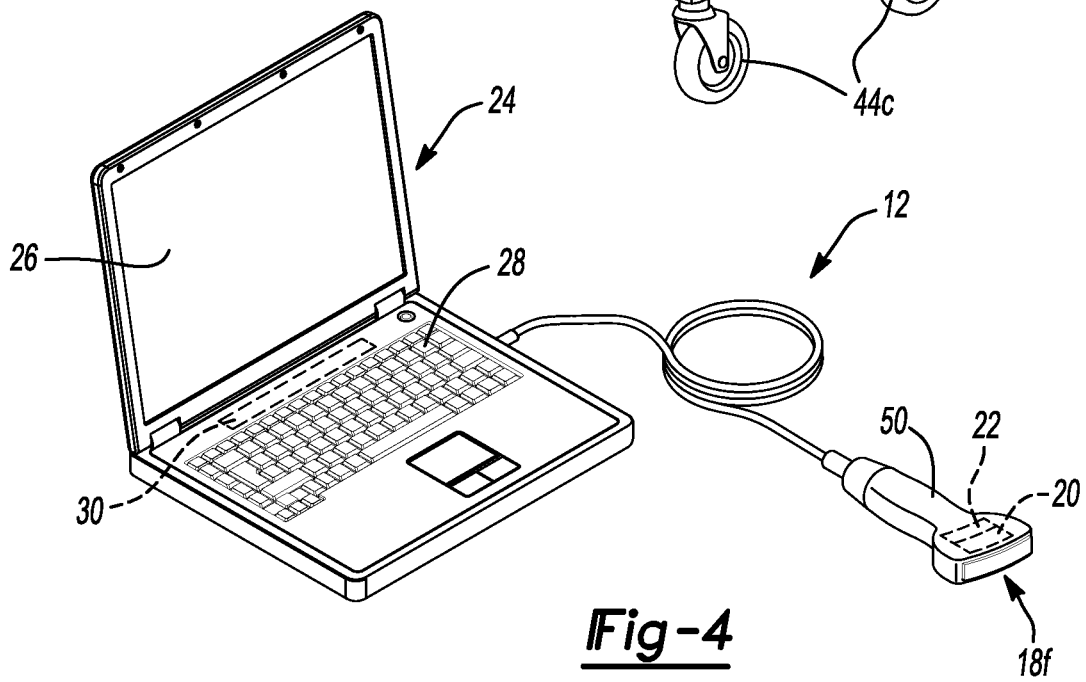
FIG. 4 is a schematic illustration of one of various embodiments for the RF imaging system of FIG. 1.

With reference to FIG. 4, in one of various examples, an imaging head 18f can be handheld. In this regard, the imaging head 18f can be coupled to a graspable portion or handle 50, which can be sized to enable an operator to manipulate the imaging head 18f with his/her hand. In one example, the RF transmitter 20 and the RF receiver 22 can be substantially contained within the handle 50. A cable 52 can enable wired communication between the imaging head 18f and the workstation 24. It should be noted that the imaging head 18f could be in wireless communication with the workstation 24, if desired.

Figure 5:
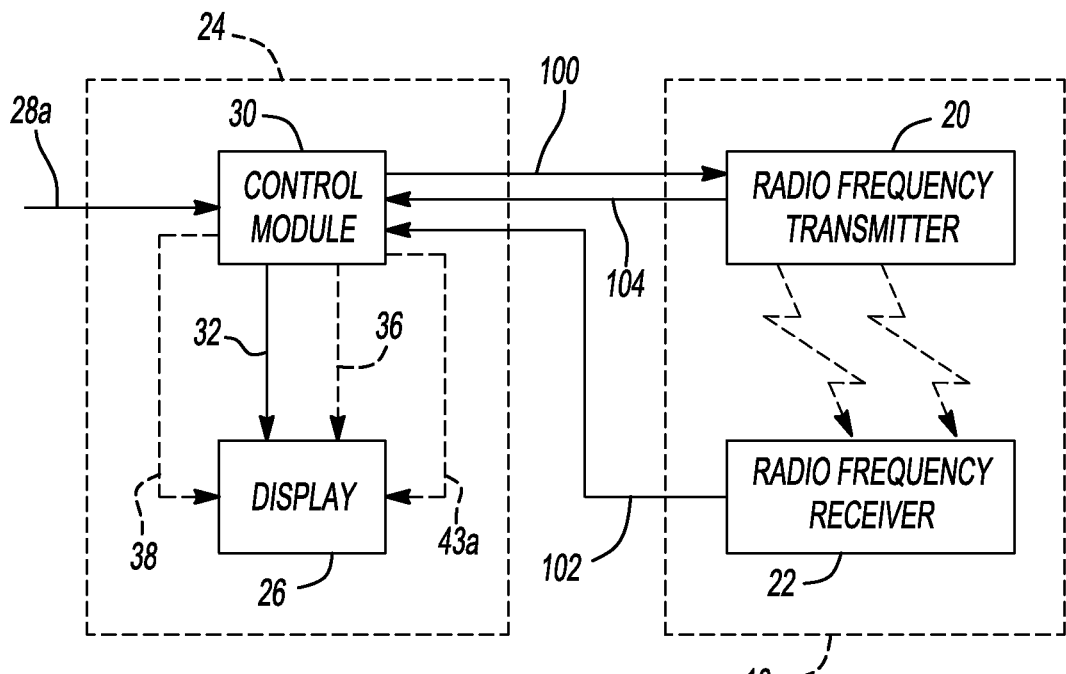
FIG. 5 is a simplified block diagram illustrating the RF imaging system of FIG. 1.

With reference to FIG. 5, a simplified block diagram schematically illustrates an exemplary RF imaging system 12 for implementing the control module 30. The RF imaging system 12 can include the imaging head 18, which can include the RF transmitter 20 and the RF receiver 22. The RF imaging system 12 can also include the workstation 24 and the display 26. The workstation 24 can receive user input data 28a. The user input data 28a can be inputted by the user input device 28, and can comprise a signal to start the imaging process using the imaging head 18. Based on the receipt of the user input data 28a, the workstation 24 can transmit a start-up signal 100 to the RF transmitter 20.

Based on the start-up signal 100, the RF transmitter 20 can emit RF energy in various ways, including in one or more signals with desired RF parameters, in the field of view F. The signal can be reflected from an object or material(s) within the field of view F, and the reflected signal can be received by the RF receiver 22. The RF receiver 22 can transmit reflected signal data 102 to the workstation 24. The reflected signal data 102 can comprise the signal reflected from the material(s).

The workstation 24 can be in communication with the RF receiver 22 to receive the reflected signal data 102, and can be in communication with the RF transmitter 20 to receive transmit signal data 104. The transmit signal data 104 can comprise an indication of the signal shape, transmitted frequency range, amplitude, and/or phase changes of transmitted RF signal. Based on the reflected signal data 102 and the transmit signal data 104, the workstation 24 can output the RF image data 32 for the display 26. The RF image data 32 can comprise a graphical representation of the material(s) encountered by the signals.

In addition, the workstation 24 can output the additional image data 36, the implant image data 38a, and/or the instrument image data 43a, which can be superimposed over the RF image data 32. As discussed, the additional image data 36 can comprise a graphical representation of the electrical properties of the material(s) encountered by the signals. The implant image data 38a can comprise a graphical representation of the implant 38 within the field of view F of the imaging head 18, based on the material(s) encountered by the signals, and can comprise an icon of the implant 38, if desired. The instrument image data 43a can comprise a graphical representation of the instrument 43 within the field of view F of the imaging head 18, based on the material(s) encountered by the signals, and can comprise an icon of the instrument 43, if desired.

Figure 6:
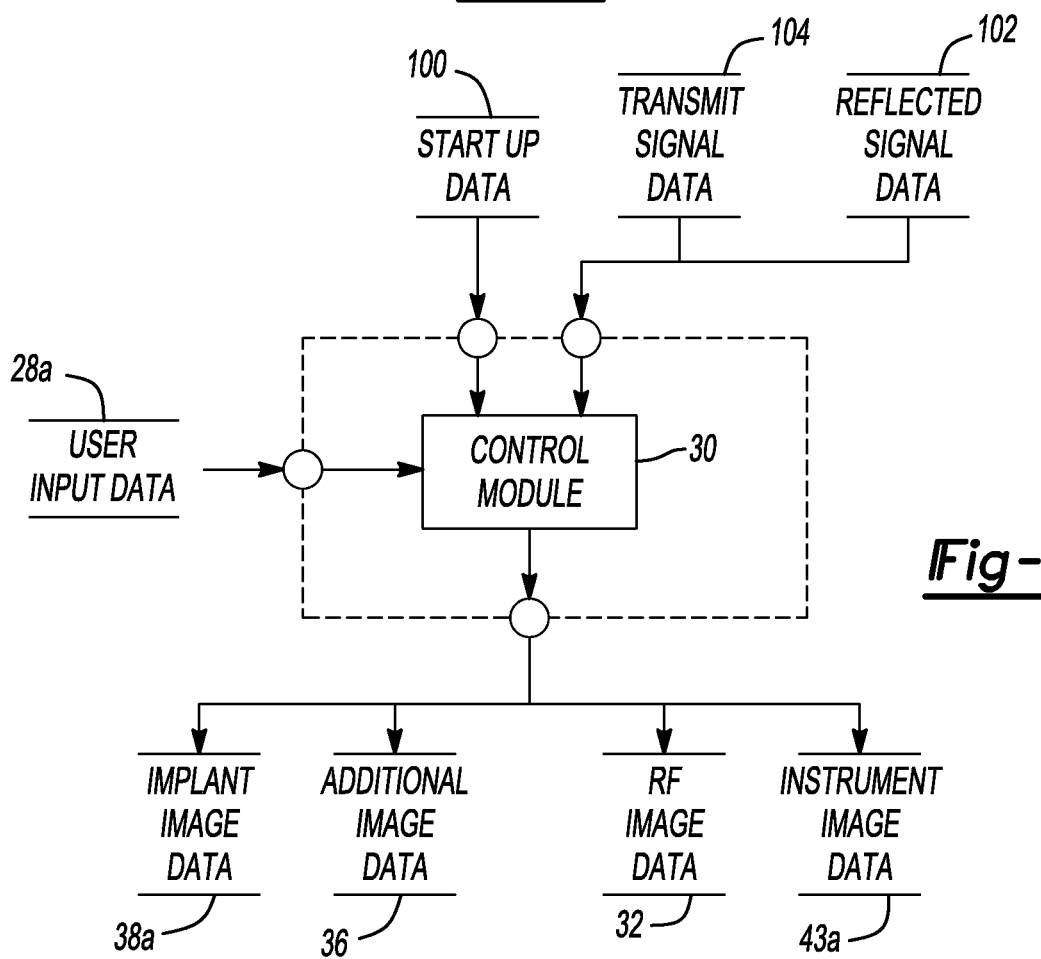
FIG. 6 is a dataflow diagram that illustrates a control system performed by a control module associated with the RF imaging system of FIG. 1.

With reference now to FIG. 6, a dataflow diagram illustrates an exemplary control system that can be embedded within the control module 30. Various embodiments of the navigation system according to the present disclosure can include any number of sub-modules embedded within the control module 30. The sub-modules shown may be combined and/or further partitioned to similarly determine the material(s) encountered by the RF signal(s), based on the transmit signal data 104 and the reflected signal data 102. In various embodiments, the control module 30 can be implemented by the workstation 24.

The control module 30 can receive as input the user input data 28a, which can comprise a signal to activate the imaging head 18. Based on the user input data 28a, the control module 30 can set start-up data 100 for the RF transmitter 20. The control module 30 can receive as input the transmit signal data 104 from the RF transmitter 20, and the reflected signal data 102 from the RF receiver 22. Given the transmit signal data 104 and the reflected signal data 102, the control module 30 can determine the material(s) encountered by the signal (s) emitted from the imaging head 18, and can output this data as RF image data 32. In addition, based on the transmit signal data 104 and the reflected signal data 102, the control module 30 can optionally determine the additional data, which can be output as additional image data 36. The control module 30 can also optionally determine if an implant 38 was encountered by the signal(s), and can output this data as the implant image data 38a. Similarly, the control module 30 can optionally determine if an instrument 43 was encountered by the signal(s), and can output this data as the instrument image data 43a.

Figure 7:
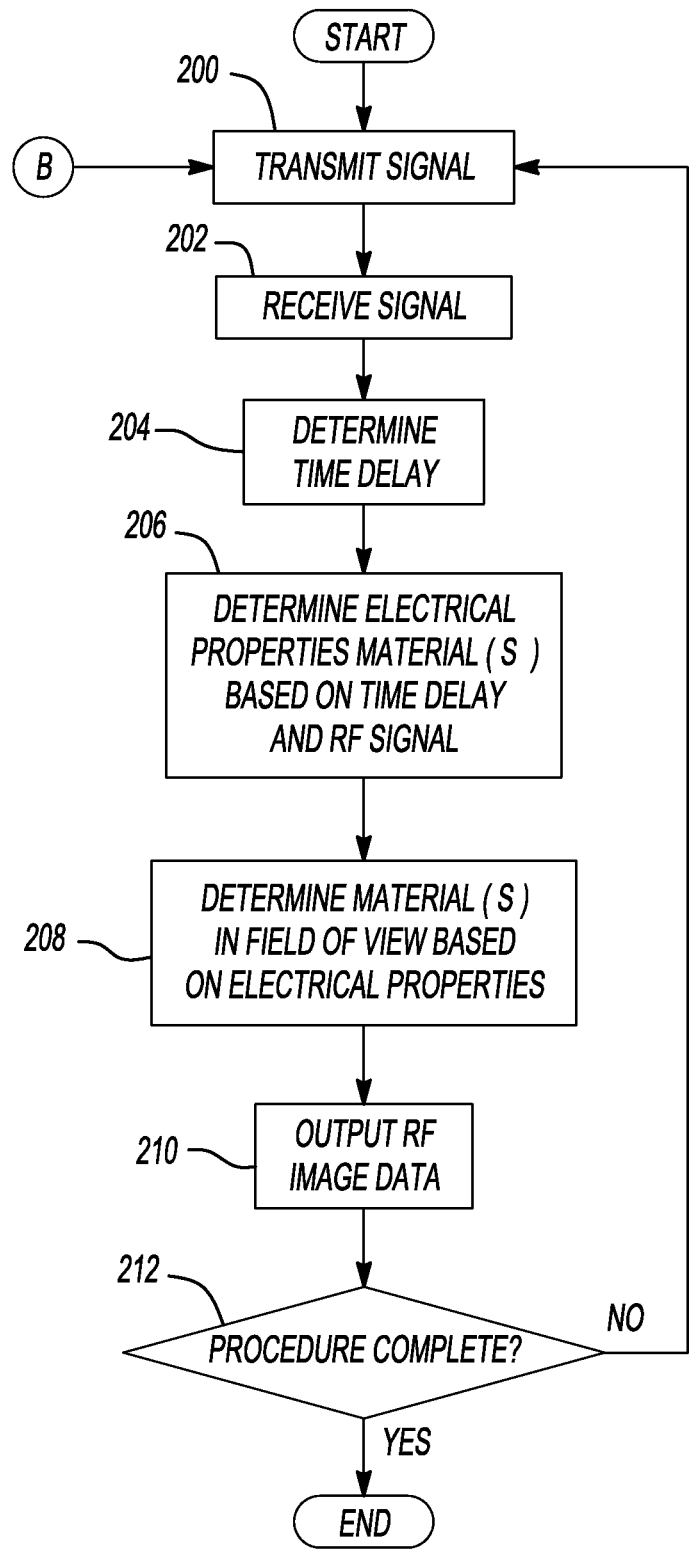
FIG. 7 is an exemplary flowchart diagram that illustrates one of various control methods performed by the control module of FIG. 6.

With reference now to FIG. 7, a flowchart diagram illustrates an exemplary method performed by the control module 30. At block 200, the method can activate the RF transmitter 20 to transmit signals into the area defined by the field of view F. At block 202, the method can receive the signals reflected back from the material(s) encountered in the field of view F via the RF receiver 22. At block 204, the method can determine the time delay between the signals transmitted by the RF transmitter 20 and received by the RF receiver 22.

At block 206, the method can determine the boundary locations and electrical properties of the material(s) within the field of view F of the imaging head 18 based on the time delay, received signal shape, received frequency bands, amplitudes, and/or phase changes of the signals. At block 208, the method can determine the boundary locations and material(s) within the field of view F of the imaging head 18 based on the dielectric properties. At block 210, the method can output RF image data 32 to the display 26. At decision block 212, the method can determine if the procedure is complete. If the procedure is not complete, then the method can loop to block 200. Otherwise, the method can end.

Navigation System Including RF Imaging System

Figure 8:
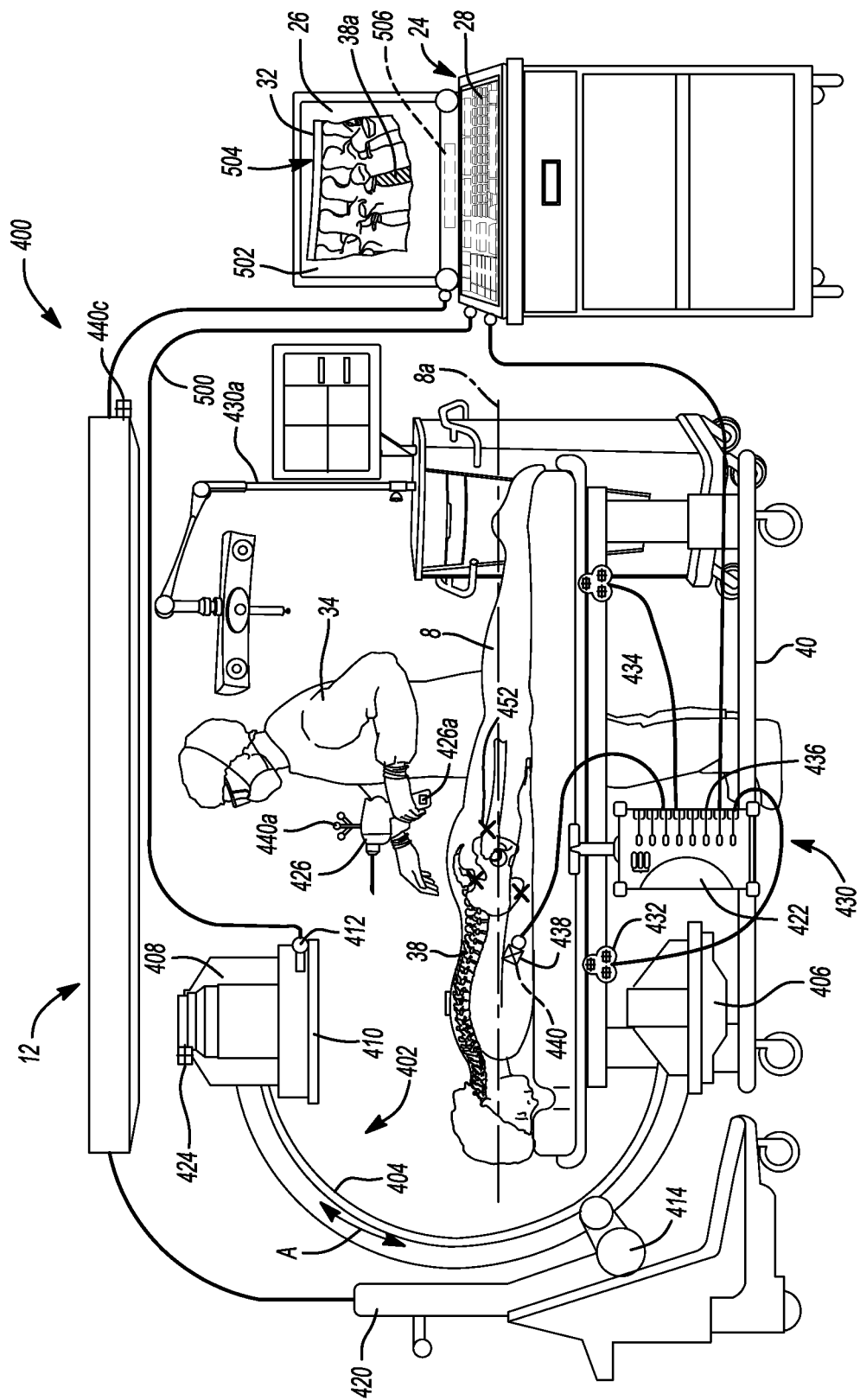
FIG. 8 is a schematic illustration of an exemplary navigation system that includes the RF imaging system of FIG. 1 for performing a surgical procedure on a patient.

FIG. 8 is a diagram illustrating an overview of a navigation system 400 that can be used for various procedures. The navigation system 400 can be used in combination with the RF imaging system 12, and thus, the same reference numerals will be used to describe the same or similar items discussed with regard to FIGS. 1-7. In addition, since the RF imaging system 12 was discussed with regard to FIGS. 1-7, the RF imaging system 12 will not be discussed in great detail herein. Briefly, however, the RF imaging system 12 can be used in combination with or can be a component of the navigation system 400. The RF imaging system 12 can provide the navigation system 400 with RF image data 32, which can be used by the navigation system 400 to register the patient 8 to the image space, track one or more instruments 426 within the body, track one or more secondary imaging fiducials, and identify one or more instruments 426, as will be discussed herein.

In addition, the navigation system 400 can be used to determine the location of the transmitter(s) and receiver(s) comprising the imaging head 18. These measurements can then be used by the RF imaging system as inputs into the generation of the RF image data 32 by the workstation 24.

With continued reference to FIG. 8, the navigation system 400 can be used with the RF imaging system 12 to track the position and orientation of various instruments. Also, the navigation system 400 can be used with the RF imaging system 12 to track the location of an implant, such as a spinal implant or orthopedic implant, relative to a patient 8. It should further be noted that the navigation system 400 can be used with the RF imaging system 12 to navigate any type of instrument, implant, or delivery system, including: guide wires, arthroscopic systems, cardiac leads, orthopedic implants, spinal implants, deep-brain stimulator (DBS)

probes, etc. relative to an anatomy. Moreover, these instruments may be used to navigate or map any region of the body. The navigation system 400, RF imaging system 12 and the various instruments may be used in any appropriate procedure, such as one that is generally minimally invasive, arthroscopic, percutaneous, stereotactic, or an open procedure.

In one example, the navigation system 400 may include a first imaging system or the RF imaging system 12, as discussed with regard to FIGS. 1-7, and a second imaging system, such as an imaging device 402. The second imaging device 402 can be used to acquire pre-, intra-, or post-operative or real-time image data of the patient 8. In one example, the optional second imaging device 402 can be, for example, a fluoroscopic x-ray imaging device that may be configured as an O-Arm™ or a C-arm 404 having an x-ray source 406, an x-ray receiving section 408, an optional calibration and tracking target 410 and optional radiation sensors 412. It will be understood, however, that the second imaging device 402 can be optional, and the patient image data can also be acquired using other imaging devices, such as those discussed further herein.

In operation, the second imaging device 402 generates x-rays from the x-ray source 406 that propagate through the patient 8 and calibration and/or tracking target 410, into the x-ray receiving section 408. This allows real-time visualization of the patient 8 and radio-opaque instruments in the cone of the X-rays. In the example of FIG. 8, a longitudinal axis 8a of the patient 8 is substantially in line with a mechanical rotational axis 414 of the C-arm 404. This can enable the C-arm 404 to be rotated relative to the patient 8, allowing images of the patient 8 to be taken from multiple directions or about multiple planes. An example of a fluoroscopic C-arm X-ray device that may be used as the optional second imaging device 402 is the "Series 9600 Mobile Digital Imaging System," from GE Healthcare, (formerly OEC Medical Systems, Inc.) of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, etc. An exemplary O-Arm™ imaging device is available from Medtronic Navigation, Inc. of Louisville, Colo.

When the x-ray source 406 generates the x-rays that propagate to the x-ray receiving section 408, the radiation sensors 412 can sense the presence of radiation, which is forwarded to an imaging device controller 420, to identify whether or not the second imaging device 402 is actively imaging. This information can also be transmitted to a coil array controller 422, further discussed herein.

The imaging device controller 420 can capture the x-ray images received at the x-ray receiving section 408 and store the images for later use. The leg that can be later used to follow contrast agent, such as Bolus tracking. The imaging device controller 420 may also be separate from the C-arm 404 and/or control the rotation of the C-arm 404. For example, the C-arm 404 can move in the direction of arrow A or rotate about the longitudinal axis 8a of the patient 8, allowing anterior or lateral views of the patient 8 to be imaged. Each of these movements involves rotation about the mechanical axis 414 of the C-arm 404. The movements of the second imaging device 402, such as the C-arm 404 can be tracked with a tracking device 424.

While the optional second imaging device 402 is shown in FIG. 1 as a C-arm 404, any other alternative 2D, 3D or 4D imaging modality may also be used. For example, any 2D, 3D or 4D imaging device, such as an O-Arm™ imaging device, isocentric fluoroscopy, bi-plane fluoroscopy, ultrasound, computed tomography (CT), multi-slice computed tomography (MSCT), magnetic resonance imaging (MRI), high frequency ultrasound (HFU), positron emission tomography (PET), optical coherence tomography (OCT), intravascular ultrasound (IVUS), ultrasound, intra-operative CT or MRI may also be used to acquire 2D, 3D or 4D pre- or post-operative and/or real-time images or patient image data 500 of the patient 8. For example, an intra-operative MRI system, may be used such as the PoleStar® MRI system sold by Medtronic, Inc.

It should further be noted that the second imaging device 402, as shown in FIG. 1, provides a virtual bi-plane image using a single-head C-arm fluoroscope as the second imaging device 402 by simply rotating the C-arm 404 about at least two planes, which could be orthogonal planes, to generate two-dimensional images that can be converted to three-dimensional volumetric images. By acquiring images in more than one plane, an icon 504 representing the location of an instrument 426, such as an impacter, stylet, reamer driver, taps, drill, deep-brain stimulator (DBS) probes, cardiac leads or other instrument, or implantable devices introduced and advanced in the patient 8, may be superimposed in more than one view and included in image data 502 displayed on the display 26, as will be discussed.

If the second imaging device 402 is employed, patient image data 500 can be forwarded from the imaging device controller 420 to a navigation computer and/or processor or workstation, such as the workstation 24. It will also be understood that the patient image data 500 is not necessarily first retained in the imaging device controller 420, but may also be directly transmitted to the workstation 24. The workstation 24 can include the display 26, the user input device 28 and a navigation control module 506. The workstation 24 can provide facilities for displaying the patient image data 500 as an image on the display 26, saving, digitally manipulating, or printing a hard copy image of the received patient image data 500.

The control module 506 can output image data 502 to the display 26. The image data 502 can include the icon 504 that provides an indication of a location of the instrument 426 with respect to the patient space, illustrated on the patient image data 500, as will be discussed herein. In addition, the image data 502 can include the RF image data 32, which can be superimposed on the patient image data 500.

With continuing reference to FIG. 8, the navigation system 400 can further include an optional electromagnetic navigation or tracking system 430. It should be noted that the tracking system 430 is optional, as the RF imaging system 12 can be used to track the position of instrument(s) 426 relative to the anatomy, if desired. If employed, the electromagnetic tracking system 430 can include a localizer, such as a first coil array 432 and/or second coil array 434, the coil array controller 422, a navigation probe interface 436, the device or instrument 426, a patient tracker or first reference frame or dynamic reference frame (DRF) 438 and one or more tracking devices 440. Other tracking systems can include an optical tracking system 430a, for example the StealthStation® Treon® and the StealthStation® Tria® both sold by Medtronic Navigation, Inc. Further, other tracking systems can be used that include acoustic, radiation, infrared, etc., or hybrid systems, such as a system that includes components of both an electromagnetic and optical tracking system, etc. The instrument 426 and the DRF 438 can each include tracking device(s) 440.

The tracking device 440 or any appropriate tracking device as discussed herein, can include both a sensor, a transmitter, or combinations thereof and can be indicated by the reference numeral 440. Further, the tracking device 440 can be wired or wireless to provide a signal or emitter or receive a signal from a system. For example, a tracking device 440 can include one or more electromagnetic coils, such as a tri-axial coil, to sense a field produced by the localizing coil array 432 or 434. In another example, a tracking device 440*a* can include or more optical receivers or transmitters for use with the optical tracking system 430*a*. One will understand that the tracking device(s) 440 can receive a signal, transmit a signal, or combinations thereof to provide information to the navigation system 400, which can be used to determine a location of the tracking device 440. The navigation system 400 can determine a position of the instrument 426 and the DRF 438 based on the location of the tracking device(s) 440 to allow for accurate navigation relative to the patient 8 in the patient space.

In the case of an electromagnetic tracking system 430, the coil arrays 432, 434 can transmit signals that are received by the tracking device(s) 440. The tracking device(s) 440 can then transmit or receive signals based upon the transmitted or received signals from or to the coil arrays 432, 434. The coil arrays 432, 434 are shown attached to the operating table 40. It should be noted, however, that the coil arrays 432, 434 can also be positioned at any other location, as well and can also be positioned in the items being navigated. The coil arrays 432, 434 include a plurality of coils that are each operable to generate distinct electromagnetic fields into the navigation region of the patient 8, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference. In addition, representative electromagnetic systems can include the AXIEM™ electromagnetic tracking system sold by Medtronic Navigation, Inc.

The coil arrays 432, 434 can be controlled or driven by the coil array controller 422. The coil array controller 422 can drive each coil in the coil arrays 432, 434 in a time division multiplex or a frequency division multiplex manner. In this regard, each coil can be driven separately at a distinct time or all of the coils can be driven simultaneously with each being driven by a different frequency. Upon driving the coils in the coil arrays 432, 434 with the coil array controller 422, electromagnetic fields are generated within the patient 8 in the area where the medical procedure is being performed, which is again sometimes referred to as patient space. The electromagnetic fields generated in the patient space induce currents in a tracking device(s) 440 positioned on or in the instrument 426, and DRF 438. These induced signals from the instrument 426 and DRF 438 are delivered to the navigation probe interface 436 and can be subsequently forwarded to the coil array controller 422.

In addition, the navigation system 400 can include a gating device or an ECG or electrocardiogram triggering device, which is attached to the patient 8, via skin electrodes, and in communication with the coil array controller 422. Respiration and cardiac motion can cause movement of cardiac structures relative to the instrument 426, even when the instrument 426 has not been moved. Therefore, patient image data 500 can be acquired from the second imaging device 402 based on a time-gated basis triggered by a physiological signal. For example, the ECG or EGM signal may be acquired from the skin electrodes or from a sensing electrode included on the instrument 426 or from a separate reference probe (not shown). A characteristic of this signal, such as an R-wave peak or P-wave peak associated with ventricular or atrial depolarization, respectively, may be used as a reference of a triggering event for the coil array controller 422 to drive the coils in the coil arrays 432, 434. This reference of a triggering event may also be used to gate or trigger image acquisition during the imaging phase with the second imaging device 402. By time-gating the image data 502 and/or the navigation data, the icon 504 of the location of the instrument 426 in image space relative to the patient space at the same point in the cardiac cycle may be displayed on the display 26. Further detail regarding the time-gating of the image data and/or navigation data can be found in U.S. Pub. Application No. 2004-0097806, entitled "Navigation System for Cardiac Therapies," filed Nov. 19, 2002, which is hereby incorporated by reference.

The navigation probe interface 436 may provide the necessary electrical isolation for the navigation system 400. The navigation probe interface 436 can also include amplifiers, filters and buffers to directly interface with the tracking device(s) 440 in the instrument 426 and DRF 438. Alternatively, the tracking device(s) 440, or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled directly to the navigation probe interface 436.

The instrument 426 may be any appropriate instrument, such as an instrument for preparing a portion of the patient 8 or an instrument for positioning an implant. The DRF 438 of the tracking system 430 can be coupled to the navigation probe interface 436. The DRF 438 may be coupled to a first portion of the anatomical structure of the patient 8 adjacent to the region being navigated so that any movement of the patient 8 is detected as relative motion between the coil arrays 432, 434 and the DRF 438. For example, as will be discussed, the DRF 438 can be adhesively coupled to the patient 8, however, the DRF 438 could also be mechanically coupled to the patient 8, if desired. The DRF 438 may include any appropriate tracking device(s) 440 used by the navigation system 400. Therefore, the DRF 438 can include an optical tracking device or acoustic, etc. If the DRF 438 is used with an electromagnetic tracking device 440*a* it can be configured as a pair of orthogonally oriented coils, each having the same centerline or may be configured in any other non-coaxial or co-axial coil configurations, such as a tri-axial coil configuration (not specifically shown).

Briefly, the navigation system 400 operates as follows. The navigation system 400 creates a translation map between all points in the radiological image generated from the second imaging device 402 in image space and the corresponding points in the anatomical structure of the patient 8 in patient space. After this map is established, whenever a tracked instrument, such as the instrument 426 is used, the workstation 24 in combination with the coil array controller 422 and the imaging device controller 420 uses the translation map to identify the corresponding point on the pre-acquired image or atlas model, which is displayed on display 26. This identification is known as navigation or localization. The icon 504 representing the localized point or instruments 426 can be shown as image data 502 on the display 26, along with the RF image data 32.

To enable navigation, the navigation system 400 must be able to detect both the position of the anatomical structure of the patient 8 and the position of the instrument 426. Knowing the location of these two items allows the navigation system 400 to compute and display the position of the instrument 426 in relation to the patient 8 on the display 26. The tracking system 430 can be employed to track the instrument 426 and the anatomical structure simultaneously, and optionally, the RF imaging system 12 can be employed with the tracking system 430 to track the instrument 426 and the anatomical structure, as will be discussed further herein.

The tracking system 430, if using an electromagnetic tracking assembly, essentially works by positioning the coil arrays 432, 434 adjacent to the patient space to generate a low-energy electromagnetic field generally referred to as a navigation field. Because every point in the navigation field or patient space is associated with a unique field strength, the tracking system 424 can determine the position of the instrument 426 by measuring the field strength at the tracking device 440 location. The DRF 438 can be fixed to the patient 8 to identify a first location of the patient 8 in the navigation field. The tracking system 424 can continuously recompute the relative position of the DRF 438 and the instrument 426 during localization and relate this spatial information to patient registration data to enable image guidance of the instrument 426 within and/or relative to the patient 8.

Patient registration is the process of determining how to correlate the position of the instrument 426 relative to the patient 8 to the position on the diagnostic or pre-acquired images. In one example, to register the patient 8, a physician or user 34 may use point registration by selecting and storing particular points from the pre-acquired images and then touching the corresponding points on the anatomical structure of the patient 8 with a pointer probe. The navigation system 400 analyzes the relationship between the two sets of points that are selected and computes a match, which correlates every point in the patient image data 500 with its corresponding point on the anatomical structure of the patient 8 or the patient space, as discussed herein. The points that are selected to perform registration are the fiducial markers 452, such as anatomical landmarks. Again, the landmarks or fiducial markers 452 are identifiable on the images, including RF images, and identifiable and accessible on the patient 8. The fiducial markers 452 can be artificial markers that are positioned on the patient 8 or anatomical landmarks that can be easily identified in the patient image data 500. The artificial landmarks can also form part of the DRF 438, such as those disclosed in U.S. Pat. No. 6,381,485, entitled "Registration of Human Anatomy Integrated for Electromagnetic Localization," issued Apr. 30, 2002, herein incorporated by reference.

The navigation system 400 may also perform registration using anatomic surface information or path information as is known in the art. The navigation system 400 may also perform 2D to 3D registration by utilizing the acquired 2D images to register 3D volume images by use of contour algorithms, point algorithms or density comparison algorithms, as is known in the art. An exemplary 2D to 3D registration procedure, is set forth in U.S. Ser. No. 10/644,680, entitled "Method and Apparatus for Performing 2D to 3D Registration" filed on Aug. 20, 2003, hereby incorporated by reference.

In one of various examples, the RF imaging system 12 can also be used by the navigation system 400 to register the patient 8 to the image space. In this regard, as discussed, the imaging head 18 can be used to determine the location and material(s) encountered by the RF signal based on the electrical properties of the encountered material(s). This can enable the detection of anatomical landmarks that are non-palpable or not detectible with other sensors due to obstruction or other limitations. For example, in the case of a pelvis, layers of fat and the position of the patient 8 may make detection of anatomical landmarks difficult for image registration. Since the RF imaging system 12 can distinguish between fat and bone, the use of the RF imaging system 12 can improve image registration. In a further example, in the case of a skull of the patient 8, with reference to FIG. 1A, the skull can have a relatively smooth surface, which can result in few unique surface landmarks. Since the RF imaging system 12 can determine a boundary, thickness or depth of various boney tissues in the skull, such as the boundary between trabecular and cortical bone, the RF imaging system 12 can provide alternative landmarks for image registration.

In order to maintain registration accuracy, with reference to FIG. 8, the navigation system 400 and/or the RF imaging system 12 continuously tracks the position of the patient 8 during registration and navigation. This is because the patient 8, DRF 438 and coil arrays 432, 434 may all move with respect to one another during the procedure, even when this movement is not desired. Alternatively the patient 8 may be held immobile once the registration has occurred, such as with a head frame (not shown). Therefore, if the navigation system 400 did not track the position of the patient 8 or area of the anatomy, any patient movement after image acquisition would result in inaccurate navigation within that image.

The DRF 438 allows the tracking system 430 to register and track the anatomy. Because the DRF 438 can be coupled to the patient 8, any movement of the anatomical structure of the patient 8 or the coil arrays 432, 434 can be detected as the relative motion between the coil arrays 432, 434 and the DRF 438. Both the relative motion of the coil arrays 432, 434 and the DRF 438 can be communicated to the coil array controller 422, via the navigation probe interface 436, which can update the registration correlation to thereby maintain accurate navigation.

It should be noted, however, that the DRF 438 can be optional. In this regard, the RF imaging system 12 can be used to track the anatomical movement of the patient 8. As the RF imaging system 12 can determine the boundaries of the material(s) encountered, if the boundaries shift, the workstation 24 can determine that anatomical movement has occurred. Based on this determination, registration can be updated to maintain accurate navigation.

In addition, with continued reference to FIG. 8, the RF imaging system 12 can be used with the navigation system 400 to identify various instruments 426 within the patient space or field of view F of the imaging head 18. In this regard, each instrument 426 can include at least one identification tag visible to the RF imaging 426*a*. The tag 426*a* can enable the imaging head 18 to identify the instrument(s) 426 within the field of view F of the imaging head 18. For example, the tag 426*a* can include a type of instrument 426, and in cases where the instrument 426 has interchangeable members, such as tips, a tag 426*a* could be associated with each of the interchangeable members to identify which tip is coupled to the instrument 426. In addition, based on the data provided by the tag 426*a*, the workstation 24 can also display a message on the display 26 if, for example, an interchangeable member is coupled to the wrong instrument 426. It should also be noted that devices, other than instruments 426, can include an tag. For example, staff, imaging systems, etc. can include tags to identify the objects to the workstation 24 via the imaging head 18.

Further, it should be noted that the imaging head 18 can be used in cooperation with the tracking system 430. In this regard, the imaging head 18 can include a tracking device 440*c*, which can enable the tracking system 430 to determine the position of the imaging head 18 within the patient space. This can allow the RF image data 32 obtained from the imaging head 18 to be placed directly into the common three-dimensional context or coordinate system used with the other objects tracked by the tracking system 430, such as the DRF 438, instrument(s) 426, etc.

In addition, the use of the tracking device 440c with the imaging head 18 can allow the registration of the RF image data 32 with tracking data obtained from the tracking system 430, and with other images, such as with the patient image data 500. In this regard, since the tracking system 430 is registered with the patient image data 500 in image space, and the position of the imaging head 18 can be determined by the tracking system 430, the images acquired by the imaging head 18 or RF image data 32, can be easily registered with the patient image data 500 in image space. This can enable the workstation 24 to provide the surgeon or user with a variety of different information regarding the patient 8.

It should also be noted that the RF imaging system 12 can be used with the navigation system 400 in place of or as a supplement to the tracking system 430. In this regard, the imaging head 18 can be used to track devices within the anatomy of the patient 8, such as implants 38 or instruments 426, as discussed with regard to FIGS. 1-7.

Figure 9:
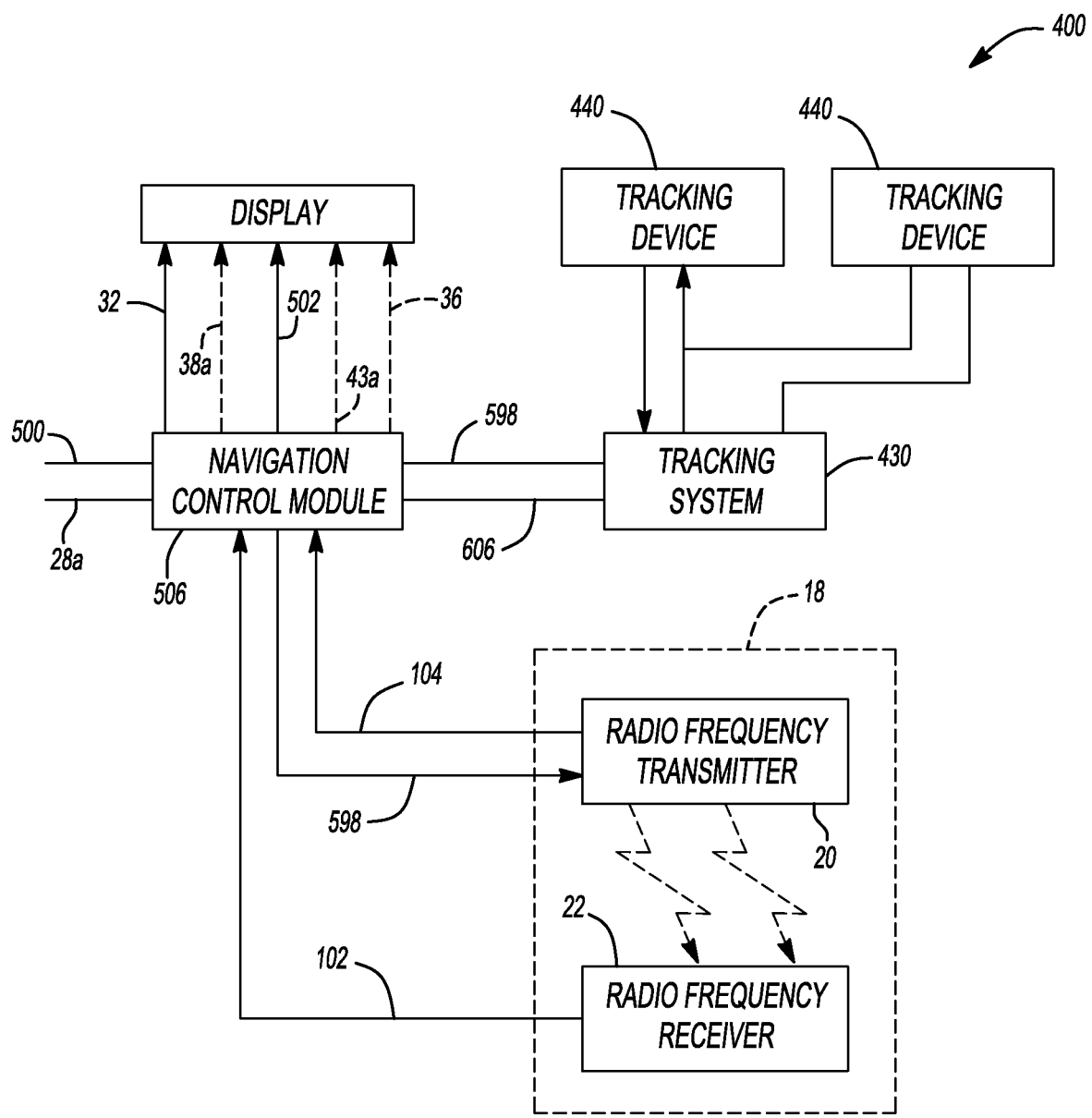
FIG. 9 is a simplified block diagram illustrating the navigation system of FIG. 8.

With reference to FIG. 9, a simplified block diagram schematically illustrates an exemplary navigation system 400 for implementing the navigation control module 506. The navigation system 400 can include the tracking system 430, the RF imaging system 12, the workstation 24 and the display 26. The tracking system 430 can comprise the electromagnetic tracking system 430 or the optical tracking system 430b, and will generally be referred to as the tracking system 430. The RF imaging system 12 can include the RF transmitter 20 and the RF receiver 22. The workstation 24 can receive user input data 28a from the user input device 28. The user input data 28a can comprise a signal to start the navigated surgical procedure using at least one of the RF imaging system 12 and the tracking system 430. Based on the receipt of the user input data 28a, the workstation 24 can transmit a start-up data 598 to the RF transmitter 20 and/or the tracking system 430.

Based on the start-up data 598, the RF transmitter 20 can emit one or more signals in the field of view F. The signals can be reflected from an object or material(s) within the field of view F, and the reflected signals can be received by the RF receiver 22. The RF receiver 22 can transmit reflected signal data 102 to the workstation 24. The reflected signal data 102 can comprise the signals reflected from the material(s) in the field of view F of the imaging head 18.

In addition, based on the start-up data 598, the tracking system 430 can set activation signal data 602. In the case of the electromagnetic tracking system 430, the activation signal data 602 can comprise a signal to activate the coil arrays 46, 47 to generate an electromagnetic field to which the tracking devices 440 coupled to the instrument 426, the DRF 438, etc. can respond.

When the tracking devices 440 are activated, the tracking devices 440 can transmit sensor data 604 indicative of a location of the tracking device 440 in the patient space to the tracking system 430. Based on the sensor data 604 received by the tracking system 430, the tracking system 430 can generate and set the tracking data 606 for the navigation control module 506. The tracking data 606 can include data regarding the coordinate locations (positions and orientations) of the objects coupled to the tracking devices 440, such as the instrument 426 and DRF 438, as computed from the sensor data 210.

The workstation 24 can be in communication with the RF receiver 22 to receive the reflected signal data 102, and can be in communication with the RF transmitter 20 to receive transmit signal data 104. The workstation 24 can also be in communication with the tracking system 430 to receive the tracking data 606. The workstation 24 can also receive patient image data 500 from the optional second imaging device 402. Based on the reflected signal data 102, the transmit signal data 104, the tracking data 606 and the patient image data 500, the workstation 24 can output the image data 502 and RF image data 32 for the display 26. The RF image data 32 can comprise a graphical representation of the material(s) encountered by the signals, which can be superimposed on the patient image data 500. In addition, as discussed with regard to FIG. 5, the workstation 24 can output the additional image data 36, the implant image data 38a, and/or the instrument image data 43a, which can be superimposed over the RF image data 32, the patient image data 500 and/or the image data 502.

Figure 10:
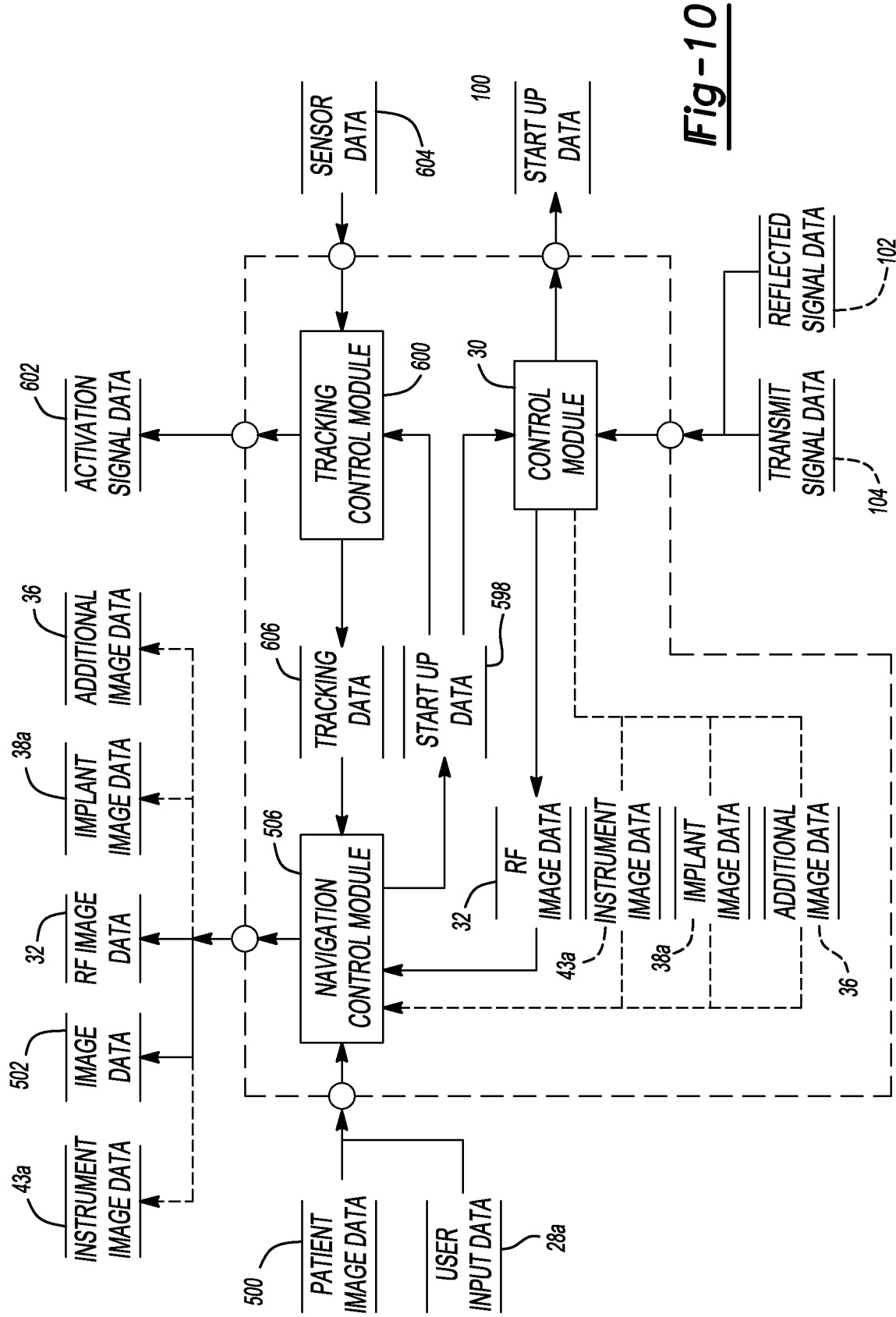
FIG. 10 is a dataflow diagram that illustrates a control system performed by a control module associated with the navigation system of FIG. 8.

With reference now to FIG. 10, a dataflow diagram illustrates an exemplary control system that can be embedded within the control module 506. Various embodiments of the navigation system according to the present disclosure can include any number of sub-modules embedded within the control module 506. The sub-modules shown may be combined and/or further partitioned to similarly facilitate a navigated surgical procedure, based on the transmit signal data 104, the reflected signal data 102 and/or the tracking data 606. In various embodiments, the control module 506 includes the tracking system 430, which can implement a tracking control module 600, and the workstation 24, which can implement the navigation control module 506 and the control module 30. It should be noted, however, that the tracking control module 600, the navigation control module 506 and the control module 30 could be implemented on the workstation 24, if desired.

The control module 30 can receive as input the user input data 28a, which can comprise a signal to activate the imaging head 18. Based on the user input data 28a, the control module 30 can set start-up data 598 for the RF transmitter 20. The control module 30 can receive as input the transmit signal data 104 from the RF transmitter 20, and the reflected signal data 102 from the RF receiver 22. Given the transmit signal data 104 and the reflected signal data 102, the control module 30 can determine the material(s) encountered by the signal(s) emitted from the imaging head 18, and can set this data as RF image data 32 for the navigation control module 506.

In addition, based on the transmit signal data 104 and the reflected signal data 102, the control module 30 can optionally determine the additional image data, which can be set as additional image data 36 for the navigation control module 506. The control module 30 can also optionally determine if an implant 38 is present in the field of view F of the imaging head 18, and can output this data as the implant image data 38a for the navigation control module 506. Similarly, the control module 30 can optionally determine if an instrument 43 is present in the field of view F of the imaging head 18, and can output this data as the instrument image data 43a for the navigation control module 506.

The tracking control module 600 can receive as input the start-up data 598 from the navigation control module 506 and sensor data 604 from the tracking device(s) 440. Upon receipt of the start-up data 598, the tracking control module 600 can output the activation signal data 602 for the tracking device(s) 440. Upon receipt of the sensor data 604, the tracking control module 600 can set the tracking data 606 for the navigation control module 506. As discussed, the tracking data 606 can include data regarding the coordinate locations (positions and orientations) of the objects coupled to the tracking device(s) 440, such as the instrument 426 and the DRF 438.

The navigation control module 506 can receive as input the RF image data 32, the user input data 28a, the tracking data 606 and the patient image data 500. Optionally, the navigation control module 506 can receive as input the additional image data 36, the implant image data 38a, and/or the instrument image data 43a from the control module 30.

Based on the RF image data 32 and the tracking data 606, the navigation control module 506 can determine the appropriate patient image data 500 for display on the display 26, and can output both the tracking data 606 and the patient image data 100 as image data 102. The navigation control module 506 can also output the RF image data 32, which can be superimposed on the image data 102 or the patient image data 500.

Figure 11:
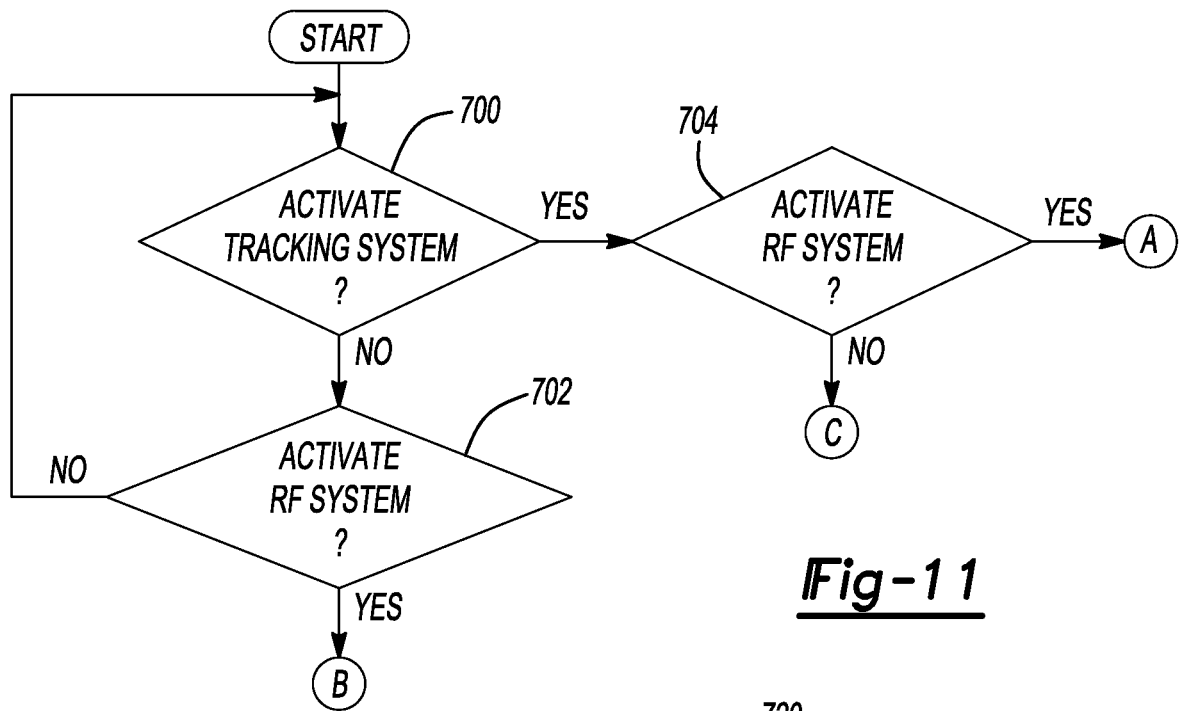
FIG. 11 is an exemplary flowchart diagram that illustrates one of various control methods performed by the control module of FIG. 10.

With reference now to FIG. 11, a flowchart diagram illustrates an exemplary method performed by the navigation control module 506. At decision block 700, the method can determine if user input data 28a has been received to activate the tracking system 430. If no user input data 28a has been received, the method can go to decision block 702. At decision block 702, the method can determine if user input data 28a has been received to activate the RF imaging system 12. If user input data 28a has been received to activate the RF imaging system 12, then the method can go to B on FIG. 7. Otherwise, the method can loop to decision block 700.

If user input data 28a has been received at decision block 600 to activate the tracking system 430, then the method can go to decision block 704. At decision block 704, the method can determine if user input data 28a has been received to activate the RF imaging system 12. If user input data 28a has been received to activate the RF imaging system 12, then the method can go to A on FIG. 13. Otherwise, the method can go to C on FIG. 12.

Figure 12:
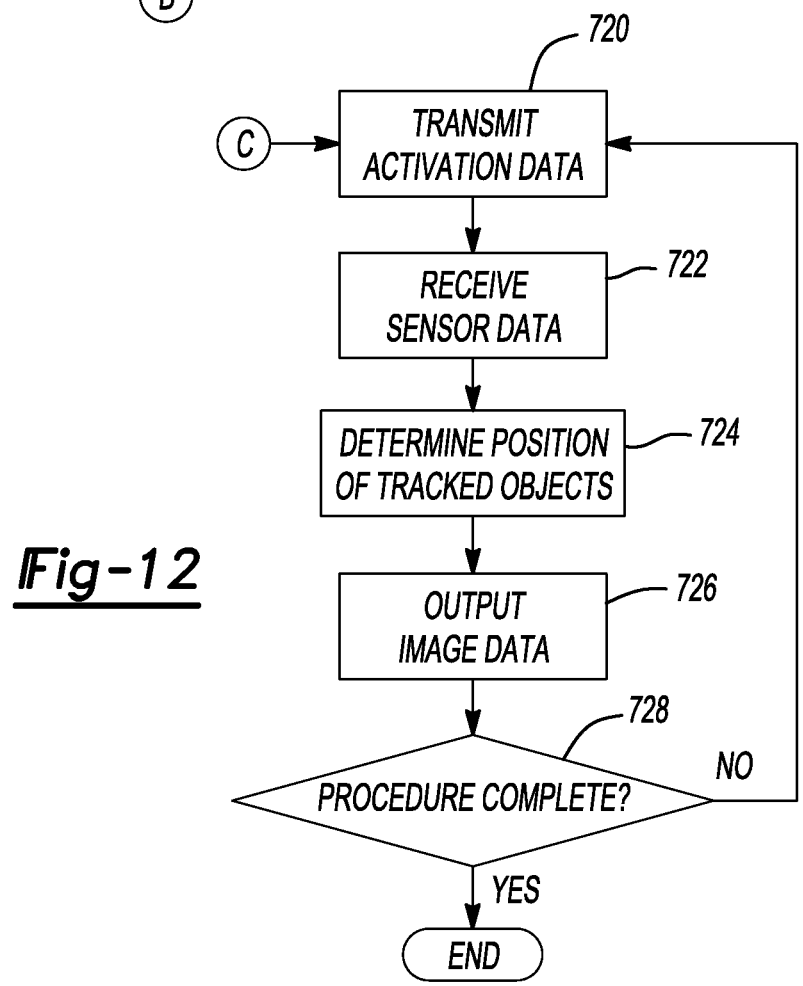
FIG. 12 is an exemplary flowchart diagram that illustrates one of various control methods performed by the control module of FIG. 10.

With reference to FIG. 12, at block 720, the method can transmit the activation signal data 602 to the tracking device(s) 440. At block 722, the method can receive sensor data 604 from the tracking device(s) 440. At block 724, the method can determine the position (location and orientation) of the objects coupled to the tracking device(s) 440, such as the instrument 426 and the DRF 438. Then, at block 726, the method can output image data 502, which can include the tracking data 606 superimposed on the patient image data 500. At decision block 728, the method can determine if the surgical procedure is complete. If the surgical procedure is complete, the method can end. Otherwise, the method can loop to block 720.

With reference to FIG. 13, at block 750, the method can transmit the activation signal data 602 to the tracking device(s) 440. At block 752, the method can activate the RF transmitter 20 to transmit signals into the area defined by the field of view F. At block 754, the method can receive sensor data 604 from the tracking device(s) 440. At block 756, the method can receive the signals reflected back from the material(s) encountered in the field of view F via the RF receiver 22. Then, at block 758, the method can determine the position (location and orientation) of the objects coupled to the tracking device(s) 440, such as the instrument 426 and the DRF 438. At block 760, the method can determine the time delay between the signals transmitted by the RF transmitter 20 and received by the RF receiver 22. Next, at block 762, the method can determine the electrical properties of the material(s) encounter by the signals based on the signal time delay and the known RF parameters of the signal. At block 764, the method can determine the material (s) encountered by the signals based on the electrical properties(s). Next, at block 766, the method can output the image data 502 and the RF image data 32. Note that the RF image data 502 can be superimposed on the image data 502 or the patient image data 500. At decision block 768, the method can determine if the procedure is complete. If the procedure is not complete, then the method can loop to block 750. Otherwise, the method can end.

While specific examples have been described in the specification and illustrated in the drawings, it will be understood by those of ordinary skill in the art that various changes may be made and equivalents may be substituted for elements thereof without departing from the scope of the present disclosure as defined in the claims. Furthermore, the mixing and matching of features, elements and/or functions between various examples is expressly contemplated herein so that one of ordinary skill in the art would appreciate from this disclosure that features, elements and/or functions of one example may be incorporated into another example as appropriate, unless described otherwise, above. Moreover, many modifications may be made to adapt a particular situation or material to the teachings of the present disclosure without departing from the essential scope thereof. Therefore, it is intended that the present disclosure not be limited to the particular examples illustrated by the drawings and described in the specification as the best mode presently contemplated for carrying out this disclosure, but that the scope of the present disclosure will include any embodiments falling within the foregoing description and the appended claims.

What is claimed is:

1. A system for determining a location of an instrument, comprising:
   an imaging head having a radio frequency transmitter configured to transmit a non-ionizing radio frequency signal and a radio frequency receiver configured to receive a non-ionizing reflected radio frequency signal used to generate an image of the instrument having at least a boundary of the instrument, wherein the non-ionizing reflected radio frequency signal is dependent on the instrument within a field of view of the imaging head;
   a tracking device associated with the imaging head, wherein the tracking device is operable to be tracked to determine a location of the imaging head; and
   a navigation system having a navigation control module configured to determine:
     based at least in part on the non-ionizing reflected radio frequency signal that generates the image of the instrument having at least the boundary of the instrument, a location of the boundary of the instrument in the field of view in a subject space defined by the subject,
     a location of the imaging head based at least on a tracked location of the tracking device, and
     both (i) a subject image for display based at least on a tracked location of the portion of the subject and (ii) superimpose the image of the instrument on the displayed subject image:
   wherein the image of the instrument is based on the non-ionizing reflected radio frequency signal from the boundary of the instrument and includes a graphical representation of the boundaries which may be based on types of material encountered by the non-ionizing reflected radio frequency signal.

2. The system of claim 1, further comprising:

a tracking system to track the tracking device;

wherein the tracking system is in communication with the navigation system to determine the location of the imaging head.

3. The system of claim 2, further comprising:

a subject tracker configured to be tracked by the tracking system to track a location of at least a portion of the subject, wherein the location of the instrument is registered to the subject with the navigation system based further at least on the tracking of the subject; and a display device configured to display at least the image of the instrument superimposed on the displayed subject image as an outline of the boundary of the instrument at the location based on the non-ionizing reflected radio frequency signal;

wherein the image can comprise at least one boundary, a shaded area, or an icon which can denote the material traversed by the non-ionizing reflected radio frequency signal.

4. The system of claim 2, wherein the boundary of the image of the instrument is determined by at least one property of at least one type of material of the instrument within a field of view of the imaging head.

5. The system of claim 4, further comprising:

a subject tracker configured to be tracked by the tracking system to track a location of at least a portion of the subject;

wherein the location of the instrument is registered to the subject with the navigation system based further at least on the tracking of the subject.

6. The system of claim 1, wherein the navigation system is configured to determine at least one type of material within a field of view of the imaging head.

7. The system of claim 1, further comprising:

a fiducial marker imageable by the imaging head and identifiable in the subject image, wherein the subject is acquired with an imaging system separate from the imaging head.

8. The system of claim 2, wherein the tracking system is at least one of an electromagnetic tracking system or an optical tracking system.

9. The system of claim 2, wherein the tracking system is in communication with the navigation system;

wherein the non-ionizing radio frequency signal includes a wavelength of about 1 centimeter to about 1 meter.

10. A system for determining a location of an instrument, comprising:

an imaging head having a radio frequency transmitter configured to transmit non-ionizing radio frequency signal and a radio frequency receiver configured to receive a non-ionizing reflected radio frequency signal from within a field of view of a subject used to generate an instrument image of the instrument able to identify at least a boundary of the instrument based at least on properties of the instrument and the non-ionizing reflected radio frequency signal;

a tracking system to track a location of at least a portion of the subject and the imaging head; and a navigation system having a processor configured to determine:

the location of the subject and the imaging head based on tracking the subject and the imaging head with the tracking system;

a subject image of the subject for display based at least on the tracked location of the portion of the subject;

a position of the instrument within the field of view relative to the subject; and superimpose the instrument image of the instrument able to identify the boundary of the instrument on the subject image at the determined position relative to the subject based on the non-ionizing reflected radio frequency signal:

wherein the instrument image is based on the non-ionizing reflected radio frequency signal from the boundary of the instrument and includes a graphical representation of the boundaries which may be based on the properties of the types of material of the instrument encountered by the non-ionizing reflected radio frequency signal.

11. The system of claim 10, further comprising:

a display device to display the subject image and illustrate the superimposed instrument image.

12. The system of claim 11, further comprising:

an imaging head tracking device configured to be tracked by the tracking system;

wherein the position of the imaging head is tracked relative to the portion of the subject and the instrument image is superimposed on the subject image based at least in part on the tracked imaging head tracking device.

13. The system of claim 12, wherein the imaging head is in communication with the navigation system to assist in maintaining registration of the subject.

14. A method of determining a location of an instrument, comprising:

transmitting a non-ionizing radio-frequency signal with a non-ionizing radio frequency transmitter;

receiving a non-ionizing reflected radio frequency signal with at least a radio frequency receiver within a field of view;

generating an instrument image including a boundary of the instrument based at least on a property of a type of material of the instrument determined with the received reflected radio frequency signal;

determining a location of the instrument within the field of view relative to a subject based on the received non-ionizing reflected radio frequency signal at the radio frequency receiver;

tracking a location of the non-ionizing radio frequency transmitter and the radio frequency receiver with a tracking device moveable with the non-ionizing radio frequency transmitter and the radio frequency receiver;

tracking a location of the subject; and determining a relative location of the instrument and the subject based at least on the tracked location of the non-ionizing radio frequency transmitter and the radio frequency receiver, the determined location of the instrument within the field of view, and the tracked location of the subject.

15. The method of claim 14, further comprising:

displaying image data of the subject based on the tracked location of the subject.

16. The method of claim 15, further comprising:
superimposing on the displayed image data of the subject the instrument image of the instrument based on the received non-ionizing reflected radio frequency signal.

17. The method of claim 14, further comprising:
placing the instrument image obtained from the radio frequency receiver directly into a common coordinate system for tracking the subject.

18. The method of claim 14, wherein tracking the location of the subject includes receiving the non-ionizing reflected radio frequency signal with at least the radio frequency receiver.

19. The method of claim 14, wherein generating the instrument image of the instrument based on the received non-ionizing reflected radio frequency signal including determining the type of instrument within the subject based at least on the received non-ionizing reflected radio frequency signal and the location of the instrument within the subject.

20. The method of claim 16, wherein the displayed image data of the subject is obtained from an imaging system separate from the radio frequency receiver;
wherein transmitting the non-ionizing radio-frequency signal includes transmitting non-ionizing radio frequency signal at a wavelength of about 1 centimeter to about 1 meter;
wherein superimposing on the displayed image data of the subject the instrument image of the instrument includes displaying a boundary of the instrument within the subject at the determined relative location.

21. The system of claim 1, wherein the imaging head is a radio-frequency imaging head which can include a reflective, transmissive, and/or scattering radio-frequency based measurement system;
wherein the navigation system having the navigation control module is further configured to generate the image of the instrument based on the received non-ionizing reflected radio frequency signal.

* * * * *

UNITED STATES PATENT AND TRADEMARK OFFICE
CERTIFICATE OF CORRECTION

| | | |
|---|---|---|
| PATENT NO. | : 10,939,053 B2 | Page 1 of 1 |
| APPLICATION NO. | : 14/269799 | |
| DATED | : March 2, 2021 | |
| INVENTOR(S) | : David A. Simon et al. | |

It is certified that error appears in the above-identified patent and that said Letters Patent is hereby corrected as shown below:

In the Specification

Column 2, Line 5, after "view", insert --.--

Column 7, Line 52, delete "18," and insert --12,-- therefor

In the Claims

Column 20, Line 65, in Claim 1, delete "image:" and insert --image;-- therefor

Column 22, Line 14, in Claim 10, delete "signal:" and insert --signal;-- therefor Signed and Sealed this
Thirty-first Day of May, 2022

*Katherine Kelly Vidal*

Katherine Kelly Vidal
*Director of the United States Patent and Trademark Office*